United States Patent
Lisanti et al.

(10) Patent No.: US 11,918,597 B2
(45) Date of Patent: *Mar. 5, 2024

(54) TRIPLE COMBINATION THERAPIES FOR ANTI-AGING

(71) Applicant: LUNELLA BIOTECH, INC., Ottawa (CA)

(72) Inventors: Michael P. Lisanti, Fulton, MD (US); Federica Sotgia, Fulton, MD (US)

(73) Assignee: LUNELLA BIOTECH, INC., Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/414,853

(22) PCT Filed: Dec. 16, 2019

(86) PCT No.: PCT/US2019/066553
§ 371 (c)(1),
(2) Date: Jun. 16, 2021

(87) PCT Pub. No.: WO2020/131704
PCT Pub. Date: Jun. 25, 2020

(65) Prior Publication Data
US 2022/0016151 A1  Jan. 20, 2022

Related U.S. Application Data

(60) Provisional application No. 62/834,794, filed on Apr. 16, 2019, provisional application No. 62/804,411, (Continued)

(51) Int. Cl.
*A61K 31/65* (2006.01)
*A61K 31/05* (2006.01)
(Continued)

(52) U.S. Cl.
CPC .......... *A61K 31/7048* (2013.01); *A61K 31/05* (2013.01); *A61K 31/166* (2013.01);
(Continued)

(58) Field of Classification Search
CPC .............. A61K 31/7048; A61K 47/542; A61K 31/375; A61K 31/65; A61K 31/7052
(Continued)

(56) References Cited

U.S. PATENT DOCUMENTS 6,805,880 B1 * 10/2004 Højgaard et al. ...... A61K 9/209
424/458
7,282,225 B1 * 10/2007 Davis .................... A61K 45/06
424/732
(Continued)

FOREIGN PATENT DOCUMENTS

CN    103536530    1/2014
SG    1120210652 W  6/2020
(Continued)

OTHER PUBLICATIONS

Lamb et al. (Oncotarget, 2015, vol. 6, No. 7, pp. 4569-4584).*
(Continued)

*Primary Examiner* — Eric Olson
(74) *Attorney, Agent, or Firm* — Nixon & Vanderhye, P.C.

(57) ABSTRACT

The present approach effectively eradicates senescent cells and cells carrying the hallmarks associated with aging, through inhibiting mitochondrial biogenesis during induced mitochondrial oxidative stress, without inhibiting normal cells. Embodiments may include a therapeutic agent that inhibits mitochondrial biogenesis and targets the large mitochondrial ribosome, a therapeutic agent that inhibits mitochondrial biogenesis and targets the small mitochondrial ribosome, and a therapeutic agent that behaves as a pro-
(Continued)

oxidant or induces mitochondrial oxidative stress. Some embodiments include sub-antimicrobial antibiotic concentrations, thereby minimizing antibiotic resistance concerns.

16 Claims, 24 Drawing Sheets

Related U.S. Application Data filed on Feb. 12, 2019, provisional application No. 62/780,488, filed on Dec. 17, 2018.

(51) Int. Cl.

| | | |
|---|---|---|
| *A61K 31/166* | (2006.01) | |
| *A61K 31/375* | (2006.01) | |
| *A61K 31/7048* | (2006.01) | |
| *A61K 31/7052* | (2006.01) | |
| *A61K 47/54* | (2017.01) | |
| *C07F 9/54* | (2006.01) | |

(52) U.S. Cl.
CPC ............ *A61K 31/375* (2013.01); *A61K 31/65* (2013.01); *A61K 31/7052* (2013.01); *A61K 47/542* (2017.08); *C07F 9/5442* (2013.01)

(58) Field of Classification Search
USPC .......................................................... 514/28
See application file for complete search history.

(56) References Cited

U.S. PATENT DOCUMENTS

| | | | |
|---|---|---|---|
| 9,180,134 B2 | 11/2015 | Auwerx et al. | |
| 2010/0099635 A1* | 4/2010 | Kellerman | A61K 45/06 514/29 |
| 2014/0199289 A1* | 7/2014 | D'Armiento | A61K 31/166 424/94.67 |
| 2015/0190415 A1* | 7/2015 | Lewis | A61K 31/4965 424/722 |
| 2022/0001015 A1* | 1/2022 | Bonner | C07D 209/08 |

FOREIGN PATENT DOCUMENTS

| | | |
|---|---|---|
| WO | 2018/170109 | 9/2018 |
| WO | 2018/195434 | 10/2018 |
| WO | WO-2018193116 A1 * | 10/2018 |
| WO | 2018/213751 | 11/2018 |

OTHER PUBLICATIONS

Carter (nam-aidsmap; Feb. 3, 2009).*
Erenpreisa et al. (Senescence, edited Volume, edited by Jolanta Dorszewska and Wojciech Kozubski, Aug. 30, 2017; Chapter 4, pp. 45-62).*
Hubackova et al. (Biological Chemistry 'Just Accepted' paper ISSN (online) 1437-4315 DOI: 10.1515/hsz-2018-0256; Published online, Sep. 29, 2018).*
Hubackova et al. (from Biological Chemistry; https://doi.org/10.1515/hsz-2018-0256; Published by De Gruyter Sep. 29, 2018 (Abstract).*
Lujambio et al., "To clear, or not to clear (senescent cells)? That is the question" Bioessays vol. 38 pp. S56-S64 DOI: 10.1002/bies.201670910 (Year: 2016).*
Zielonka et al., "Mitochondria-Targeted Triphenylphosphonium-Based Compounds: Syntheses, Mechanisms of Action, and Therapeutic and Diagnostic Applications" Chemical Reviews vol. 117 pp. 10043-10120 (Year: 217).*
Fuentes-Retamal et al., "Complex Mitochondrial Dysfunction Induced by TPP+-Gentisic Acid and Mitochondrial Translation Inhibition by Doxycycline Evokes Synergistic Lethality in Breast Cancer Cells" Cells vol. 9 p. 407 doi: 10.3390/cells9020407 (Year: 2020).*
Gasek et al., "Strategies for targeting senescent cells in human disease" Nature Aging vol. 1 pp. 870-879 https://doi.org/10.1038/s43587-021-00121-8 (Year: 2021).*
Katzir et al., "Senescent cells and the incidence of age-related diseases" Aging Cell vol. 20 e13314 DOI:10.1111/acel.13314 (Year: 2021).*
Marco Fiorillo, et al., "Doxycycline, Azithromycin and Vitamin C (DAV): A potent combination therapy for targeting mitochondria and eradicating cancer stem cells (CSCs)", Aging, vol. 11, No. 8, Apr. 19, 2019, pp. 2202-2216 (15 pages).
Ernestina Marianna De Francesco, et al., "Vitamin C and Doxycycline: A synthetic lethal combination therapy targeting metabolic flexibility in cancer stem cells (CSCs)", Oncotarget, vol. 8, No. 40, Jun. 9, 2017, pp. 67269-67286 (18 pages).
"Antibiotics eliminate senescent cells associated with ageing", University of Salford, MedicalXpress, Nov. 28, 2018, 3 pages.
International Search Report and Written Opinion of the ISA for PCT/US2019/066553 dated Mar. 5, 2020, 14 pages.

* cited by examiner

TRIPLE COMBINATION THERAPIES FOR ANTI-AGING

This application is the U.S. national phase of International Application No. PCT/US2019/066553 filed Dec. 16, 2019 which designated the U.S. and claims priority to U.S. Provisional Patent Application Nos. 62/780,488 filed Dec. 17, 2018, 62/804,411 filed Feb. 12, 2019, and 62/834,794 filed Apr. 16, 2019, the entire contents of each of which are hereby incorporated by reference.

FIELD

The present disclosure relates to compositions and methods for anti-aging, among other beneficial therapeutic uses.

BACKGROUND

The biological process of aging continues to receive significant attention in the scientific and medical research communities. Physiologic aging relates, at least in part, to an increase in the rate of oxidative damage to cellular components, including DNA, lipids, proteins, and the like. The increased oxidative damage creates an imbalance that disrupts self-regulating processes at the cellular level. Further, aging correlates to an accumulation of lipofuscin in neuron cytoplasm. Modern research also indicates that aging is a consequence of naturally occurring DNA damage, resulting in abnormal DNA alterations, accumulating over time. Both mitochondrial and nuclear DNA damage can contribute to aging, indirectly through increasing apoptosis and cellular senescence, and directly by increasing cell dysfunction. Accumulated DNA damage can lead to loss of cells and, in surviving cells, loss of gene expression and mutation—effects that, in infrequently dividing cells, produce indicia of aging. With respect to frequently dividing cells, accumulated DNA damage can become a prominent cause of cancer.

Aging also increases the likelihood of developing cancer, and researchers have struggled to develop new anti-cancer treatments. Conventional cancer therapies (e.g. irradiation, alkylating agents such as cyclophosphamide, and anti-metabolites such as 5-Fluorouracil) have attempted to selectively detect and eradicate fast-growing cancer cells by interfering with cellular mechanisms involved in cell growth and DNA replication. Other cancer therapies have used immunotherapies that selectively bind mutant tumor antigens on fast-growing cancer cells (e.g., monoclonal antibodies). Unfortunately, tumors often recur following these therapies at the same or different site(s), indicating that not all cancer cells have been eradicated. Cancer stem cells, in particular, survive for various reasons, and lead to treatment failure. Relapse may be due to insufficient chemotherapeutic dosage and/or emergence of cancer clones resistant to therapy. Hence, novel cancer treatment strategies are needed that overcome the deficiencies of conventional therapies.

Advances in mutational analysis have allowed in-depth study of the genetic mutations that occur during cancer development. Despite having knowledge of the genomic landscape, modern oncology has had difficulty with identifying primary driver mutations across cancer subtypes. The harsh reality appears to be that each patient's tumor is unique, and a single tumor may contain multiple divergent clone cells. What is needed, then, is a new approach that emphasizes commonalities between different cancer types. Targeting the metabolic differences between tumor and normal cells holds promise as a novel cancer treatment strategy. An analysis of transcriptional profiling data from human breast cancer samples revealed more than 95 elevated mRNA transcripts associated with mitochondrial biogenesis and/or mitochondrial translation. Sotgia et al., *Cell Cycle*, 11(23):4390-4401 (2012). Additionally, more than 35 of the 95 upregulated mRNAs encode mitochondrial ribosomal proteins (MRPs). Proteomic analysis of human breast cancer stem cells likewise revealed the significant overexpression of several mitoribosomal proteins as well as other proteins associated with mitochondrial biogenesis. Lamb et al., *Oncotarget*, 5(22):11029-11037 (2014).

Functional inhibition of mitochondrial biogenesis using the off-target effects of certain bacteriostatic antibiotics or OXPHOS inhibitors provides additional evidence that functional mitochondria are required for the propagation of cancer stem cells. The inventors recently showed that a mitochondrial fluorescent dye (MitoTracker) could be effectively used for the enrichment and purification of cancer stem-like cells from a heterogeneous population of living cells. Farnie et al., *Oncotarget*, 6:30272-30486 (2015). Cancer cells with the highest mitochondrial mass had the strongest functional ability to undergo anchorage-independent growth, a characteristic normally associated with metastatic potential. The 'Mito-high' cell sub-population also had the highest tumor-initiating activity in vivo, as shown using pre-clinical models. The inventors also demonstrated that several classes of non-toxic antibiotics could be used to halt cancer stem cell (CSC) propagation. Lamb et al., *Oncotarget*, 6:4569-4584 (2015). Because of the conserved evolutionary similarities between aerobic bacteria and mitochondria, certain classes of antibiotics or compounds having antibiotic activity can inhibit mitochondrial protein translation as an off-target side-effect. Contemporary medicine generally views anti-mitochondrial side-effects as undesirable, and often those off-target consequences result in using a different drug.

What is needed, then, are novel anti-aging compositions and methods that treat aging at the cellular level, overcoming accumulated oxidative and DNA damage and the numerous undesired effects of aging.

SUMMARY

In view of the foregoing background, it is an object of the present approach to provide compositions and methods for slowing the effects of aging, and in many instances reverse certain effects of aging. The compositions and methods of the present approach may overcome the impact of accumulated oxidative and DNA damage, and quell many of the side effects associated with aging. The present approach may also be used for treating and/or reducing the effects of aging. Embodiments may be used for, as an example, improving health-span and life-span.

Embodiments of the present approach induce a mitochondrial catastrophe in senescent cells, through inhibiting mitochondrial biogenesis during induced mitochondrial oxidative stress. According to some embodiments of the present approach, a first antibiotic inhibiting the large mitochondrial ribosome, and a second antibiotic inhibiting the small mitochondrial ribosome, may be administered with a pro-oxidant or an agent inducing mitochondrial oxidative stress. In some embodiments, one or more FDA-approved antibiotics may be used in connection with one or more common dietary supplements. The pro-oxidant may be, in some embodiments, a therapeutic agent having a pro-oxidant effect. For example, the pro-oxidant may be a therapeutic agent at a concentration that causes the therapeutic agent to act as a reducing agent. In some embodiments, one or more therapeutic agents may be conjugated with a targeting signal. Embodiments of the present approach may be used for one or more of slowing the effects of aging, as well as reversing many of those effects. In addition to anti-aging, the present approach may be used for treating and/or preventing cancer, tumor recurrence, metastasis, chemotherapy or drug resistance, radiotherapy resistance, and cachexia, due to cancer or other causes, among other beneficial therapies. The mechanism of the present approach similarly targets senescent cells, and may have an advantageous impact on the disposition of accumulated DNA damage. For instance, azithromycin is an anti-aging drug that behaves as a senolytic, which selectively kills and removes senescent fibroblasts.

Some embodiments may be used to advantageously target and kill senescent cells over normal, healthy cells. In some embodiments, the composition prevents acquisition of a senescence-associated secretory phenotype. In some embodiments, the composition facilitates tissue repair and regeneration. In some embodiments, the composition increases at least one of organismal life-span and healthspan. In some embodiments, the present approach may reduce one or more of hair loss, hearing loss, vision loss, memory loss, mental slowness, joint stiffness, muscle loss, strength loss, speed loss, balance loss, endurance loss, agility loss, sexual dysfunction, virility loss, testosterone reduction, lipofuscin deposits, and inflammation. The present approach may improve and/or increase one or more of hair regeneration, hearing, vision, memory, mental acuity, joint mobility, muscle growth, muscular strength, muscular endurance, speed, balance, agility, and sexual performance. For example, the present approach has the potential to restore hair growth and natural hair color, restore muscular coordination and gait, restore overall mobility, increase muscle mass, increase grip strength, increase concentration ability and mental clarity, increase learning and memory, and result in an overall feeling of well-being and positive energy in mammals that would otherwise suffer from aging side-effects. Some embodiments of the present approach have demonstrated a reduction in gray hair, overall frailty, forgetfulness, and general aches and pains. Additional studies and trials are underway to more thoroughly understand and quantify the benefits of the compositions and methods of the present approach.

The anti-aging activity of the present approach is related to the anti-cancer efficacy of the present approach. CSCs are hyper-metabolic, and as disclosed in related applications, hindering CSC metabolic activity is an effective strategy for eradicating CSCs. Senescent cells may have a similar metabolic weakness. In a demonstrative anti-cancer embodiment, the combination of doxycycline, azithromycin, and vitamin C effectively targets the mitochondria and potently inhibits CSC propagation. Cancer stem cells are metabolically hyperactive relative to normal cells, due at least in part to the elevated quantity of mitochondria in cancer stem cells, and therefore this approach selectively targets the CSC population. Azithromycin inhibits the large mitochondrial ribosome as an off-target side-effect. In addition, Doxycycline inhibits the small mitochondrial ribosome as an off-target side-effect. Vitamin C acts as a mild pro-oxidant, which can produce free radicals and, as a consequence, induces mitochondrial biogenesis. Remarkably, treatment with a combination of Doxycycline (1 µM), Azithromycin (1 µM) plus Vitamin C (250 µM) according to one embodiment of the present approach very potently inhibited CSC propagation by ~90%, using the MCF7 ER(+) breast cancer cell line as a model system. The strong inhibitory effects of this triple combination therapy on mitochondrial oxygen consumption and ATP production were directly validated using metabolic flux analysis. Therefore, the induction of mild mitochondrial oxidative stress, coupled with an inhibition of mitochondrial biogenesis, represents an effective therapeutic anti-cancer strategy. Consistent with these assertions, Vitamin C is known to be highly concentrated within mitochondria, by a specific transporter, namely SCVCT2, in a sodium-coupled manner. Compositions according to one embodiment of the present approach have inhibited CSC propagation by ~90% in MCF7 ER(+) cell lines during preliminary studies, with confirmed reduction in mitochondrial oxygen consumption and ATP production. Further, some embodiments may use sub-antimicrobial antibiotic concentrations, thereby minimizing or avoiding antibiotic resistance concerns—a significant benefit to the medical community.

The present approach may, in some embodiments, take the form of a composition having (i) a member of the erythromycin family, (ii) a member of the tetracycline family, and (iii) a pro-oxidant. In some of the embodiments discussed below, the composition included azithromycin, doxycycline, and Vitamin C, as the therapeutic agents. Azithromycin is a widely-used antibiotic, and has an often-undesired side-effect of inhibiting the large mitochondrial ribosome. Doxycycline inhibits the small mitochondrial ribosome, also an undesired side-effect. These off-target effects frequently cause physicians to select other drugs for various indications. The present approach, however, makes advantageous use of such off-target mitochondrial inhibition effects, to selectively target and eradicate senescent cells and CSCs. Vitamin C acts as a mild pro-oxidant in certain situations, and as a pro-oxidant induces mitochondrial oxidative stress in senescent cells and CSCs through the production of free radicals and reactive oxygen species. (It should be noted that other ascorbate derivatives may have similar pro-oxidant effects, particularly at low concentrations.) These cells respond to mitochondrial oxidative stress through mitochondrial biogenesis. However, in the presence of mitochondrial biogenesis inhibitors such as azithromycin and doxycycline, these cells are unable to adapt to and survive the induced mitochondrial oxidative stress. The present approach is selective, targeting senescent cells and CSCs while having little, if any, impact on normal, healthy cells.

In an example embodiment for anti-aging, treatment according to the present approach was prescribed over a recurring cycle. The composition included azithromycin as the first antibiotic inhibiting the large mitochondrial ribosome, doxycycline as the second antibiotic inhibiting the small mitochondrial ribosome, and Vitamin C as a pro-oxidant for inducing mitochondrial oxidative stress. Over a five-week period, azithromycin was administered at 250 mg twice per week, doxycycline was administered at 100 mg twice per day, and Vitamin C was administered at 500 mg once per day. The subject—a 77-year old male—reported increased hair growth, mental awareness and acuity, strength and stamina, and sexual drive, as well as improved vision, hearing, speech, coordination and balance, an overall feeling of well-being and positive energy. The recipient also reported the disappearance of a clinically-palpable prostate nodule following treatment according to the present approach, without any other medications or changes in diet, exercise, and routine.

In an example embodiment for anti-cancer, treatment with a combination of doxycycline (at 1 µM), azithromycin (at 1 µM), and Vitamin C (at 250 µM), inhibited CSC propagation in MCF7 ER(+) breast cancer cells, by ~90%. The strong inhibitory effects of this triple combination therapy on mitochondrial oxygen consumption and ATP production have been directly validated using metabolic flux analysis. The induction of mild mitochondrial oxidative stress, coupled with an inhibition of mitochondrial biogenesis, as described herein, represents a potent anti-cancer therapy. Also, the sub-antimicrobial antibiotic concentrations used in the examples discussed herein may raise little, if any, concerns relating to the development of antibiotic resistance. Thus, in some embodiments, a first antibiotic inhibiting the large mitochondrial ribosome, and/or a second antibiotic inhibiting the small mitochondrial ribosome may be administered in sub-antimicrobial concentrations. For example, a common sub-antimicrobial dose of doxycycline is 20 mg, which may be suitable in some embodiments of the present approach. As another example, an amount of doxycycline sufficient to generate a peak doxycycline concentration of about 1 μM in at least one of blood, serum, and plasma, may be sufficient in some embodiments. As another example, a common oral sub-antimicrobial dose of azithromycin is 250 mg, which may be suitable in some embodiments of the present approach. As yet another example, an amount of azithromycin sufficient to generate a peak azithromycin concentration of about 1 μM in at least one of blood, serum, and plasma, may be sufficient in some embodiments. It should be appreciated that optimization may require further refinement for a particular embodiment, but that such refinement is within the level of ordinary skill in the art.

FDA-approved antibiotics, and in particular tetracycline family members, such as doxycycline, and erythromycin family members, such as azithromycin, have off-target effects of inhibiting mitochondrial biogenesis. When used alone, however, antibiotics having anti-mitochondrial properties do not guarantee eradication of all senescent cells or CSCs. Combinations of one or more therapeutic agents that target the large mitochondrial ribosome with one or more therapeutic agents that target the small mitochondrial ribosome are more effective, as demonstrated herein. There may be, however, a metabolic shift in surviving cell sub-populations following exposure to mitochondrial biogenesis inhibitors, from oxidative metabolism to glycolytic metabolism, resulting in metabolic inflexibility. Pro-oxidant compounds, on the other hand, induce mitochondrial oxidative stress that shifts these cells towards mitochondrial biogenesis. The dual approach of inducing mitochondrial oxidative stress while inhibiting mitochondrial biogenesis leaves these cells with no alternative survival mechanisms. As a result, the triple combination of a therapeutic agent that targets the large mitochondrial ribosome, with a therapeutic agent that targets the small mitochondrial ribosome, and a pro-oxidant, enables a highly potent anti-aging and anti-cancer strategy.

In some preferred embodiments, the anti-cancer triple combination includes a first antibiotic inhibiting the large mitochondrial ribosome, and a second antibiotic inhibiting the small mitochondrial ribosome, and a pro-oxidant. In some preferred embodiments, the triple combination includes at least one antibiotic from the tetracycline family, at least one antibiotic from the erythromycin family, and Vitamin C. Advantageously, some embodiments of the present approach call for antibiotic concentrations in sub-antimicrobial doses. For example, doxycycline and azithromycin may be administered at sub-antimicrobial doses as known in the art for a given dosage form, such as orally at 20 mg for doxycycline, and orally at 250 mg for azithromycin. As another example, doxycycline and azithromycin may be administered sufficient to cause a peak doxycycline concentration of about 0.05 μM to about 5 μM in some embodiments, and 0.5 μM to about 2.5 μM in some embodiments, and about 1 μM in some embodiments, in at least one of blood, serum, and plasma. Further evaluations of suitable dosing for various embodiments are underway, and it should be appreciated that other amounts and concentrations may be used without departing from the present approach.

Described herein are examples of anti-aging compositions, compounds and methods. The present approach may be used as an anti-aging therapy, to overcome various effects of aging, and may be used in connection with other therapies, such as anti-cancer chemotherapy and/or radiotherapy. For example, the present approach may be used prior to, during, and/or following, surgical tumor removal, to prevent or reduce the likelihood of metastasis. As another example, the present approach may be used before, during, or following, chemotherapy, to enhance the likelihood of success. As another example, the present approach may be used on a recurring basis (e.g., yearly), to sustain the benefits and decrease the onset of aging side-effects. The recurring basis may also beneficially prevent and/or reduce the likelihood of recurrence and/or metastasis. In addition to senescent cells, embodiments of the present approach may be used to target cancer stem cells, thereby directly addressing the potential for tumor recurrence, metastasis, drug resistance, and/or radiotherapy resistance. For example, the target cancer cell phenotype may be at least one of a CSC, an energetic cancer stem cell (eCSC), a circulating tumor cell (CTC), and a therapy-resistant cancer cell (TRCC).

Further, the anti-mitochondrial properties of an antibiotic may be enhanced by chemically modifying the antibiotic with one or more membrane-targeting signals and/or mitochondria-targeting signals. For example, fatty acid targeting signals may be conjugated with an antibiotic and result in a compound having improved efficacy under the present approach. A therapeutic agent may be conjugated with a lipophilic cation, such as a TPP moiety, and have improved mitochondrial uptake and CSC inhibition activity. Embodiments of doxycycline-myristate conjugates, for instance, show better CSC inhibitory properties and less toxicity than doxycycline. Similar results have been fond with other tetracycline and erythromycin family members conjugated with a fatty acid, and also conjugated with TPP. Demonstrative examples are discussed below. See, for example, the approaches disclosed in International Patent Application PCT/US2018/033466, filed May 18, 2018, International Patent Application PCT/US2018/062174, filed Nov. 21, 2018, and International Patent Application PCT/US2018/062956, filed Nov. 29, 2019, each of which is incorporated herein by reference in its entirety. The addition of one or more targeting signals to a therapeutic agent can significantly increase the effectiveness of that agent, in some instances by over 100 times in the target organelle. Thus, some embodiments of the present approach may have one or more therapeutic agents chemically modified with a targeting signal. Such modification may allow for smaller concentrations or doses, another advantageous benefit of the present approach.

Examples of membrane-targeting signals include fatty acids such as palmitic acid, stearic acid, myristic acid, oleic acid, short chain fatty acids (i.e., having 5 or fewer carbon atoms in the chemical structure), medium-chain fatty acids (having 6-12 carbon atoms in the chemical structure), and other long chain fatty acids (i.e., having 13-21 carbon atoms in the chemical structure). This disclosure may interchangeably refer to these targeting signals as their salt or ester forms (e.g., myristic acid, myristate, tetradecanoate), and it should be appreciated that the carboacyl of the fatty acid may be attached by an amide bond to the therapeutic agent. For example, the myristoylation process known in the art for forming myristoylated proteins may be used to form a therapeutic agent according to the present approach. Examples of mitochondria-targeting signals include lipophilic cations such as tri-phenyl-phosphonium (TPP), TPP-derivatives, guanidinium, guanidinium derivatives, and 10-N-nonyl acridine orange. A carbon spacer arm and/or linking group may be used to tether the mitochondria-targeting signal to the therapeutic agent. It should be appreciated that these examples are not intended to be exhaustive.

The present disclosure may take the form of one or more pharmaceutical compositions. The composition may be for treating and/or preventing one or more of aging, age-related side-effects, cancer, drug resistance in cancer cells, chemotherapy resistance in cancer cells, tumor recurrence, metastasis, and radiotherapy resistance. In particular, the present approach may be used to delay the onset of senescence. Embodiments of the present approach may be used for the manufacture of pharmaceutical compositions for one or more of treating senescence, preventing senescence, and/or delaying the onset of senescence. Some embodiments may have one or more of anti-viral activity, anti-bacterial activity, anti-microbial activity, photosensitizing activity, and radiosensitizing activity. Some embodiments may sensitize cancer cells to chemotherapeutic agents, sensitize cancer cells to natural substances, and/or sensitize cancer cells to caloric restriction.

In some embodiments, the present disclosure relates to treatment methods comprising administering to a patient in need thereof of a pharmaceutically effective amount of a one or more pharmaceutical compositions and a pharmaceutically acceptable carrier. In some embodiments, the third agent may be replaced with a chemotherapeutic agent or radiation therapy that drives the production of reactive oxygen species and/or mitochondrial oxidative stress. In such embodiments, for example, the mitochondrial inhibitors may be used in combination with chemotherapy or radiation treatment, to reduce the incidence of tumor recurrence, metastasis and treatment failure, via their ability to inhibit mitochondrial biogenesis and prevent CSC propagation. In some embodiments, for example, the combination of a first antibiotic inhibiting the large mitochondrial ribosome, and a second antibiotic inhibiting the small mitochondrial ribosome, may be administered in conjunction with traditional chemotherapy to reduce or prevent recurrence and/or metastasis. Methods include reducing and/or eliminating age-related side effects, including improving one or more of numerous effects of aging. Additionally, the present approach may be used in methods to slow the onset of aging and age-related side effects.

DESCRIPTION

Figure 1A:
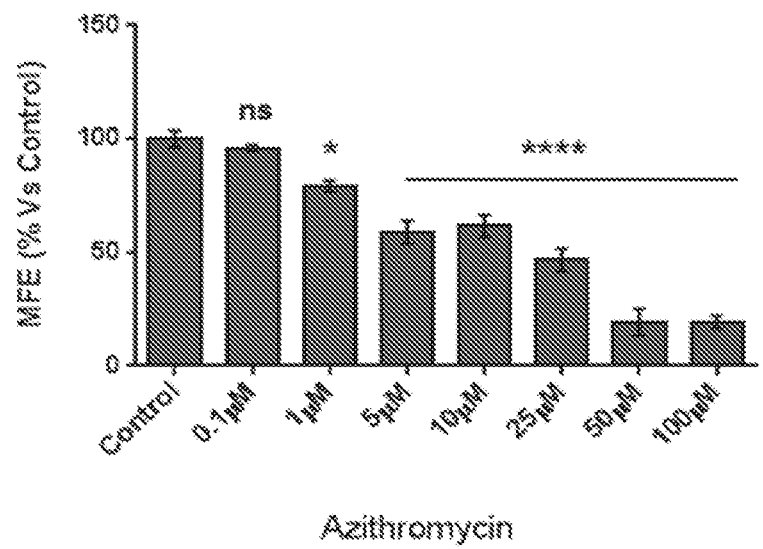
FIGS. 1A-1C summarize mammosphere formation data for varying concentrations and combinations of doxycycline and azithromycin.

The following description illustrates embodiments of the present approach in sufficient detail to enable practice of the present approach. Although the present approach is described with reference to these specific embodiments, it should be appreciated that the present approach can be embodied in different forms, and this description should not be construed as limiting any appended claims to the specific embodiments set forth herein. Rather, these embodiments are provided so that this disclosure will be thorough and complete, and will fully convey the scope of the present approach to those skilled in the art.

This description uses various terms that should be understood by those of an ordinary level of skill in the art. The following clarifications are made for the avoidance of doubt. As used herein, the term derivative is a chemical moiety derived or synthesized from a referenced chemical moiety. As used herein, a conjugate is a compound formed by the joining of two or more chemical compounds. For example, a conjugate of doxycycline and a fatty acid results in a compound having a doxycycline moiety and a moiety derived from the fatty acid As used herein, a fatty acid is a carboxylic acid with an aliphatic chain, which is either saturated or unsaturated. Examples of fatty acids include short chain fatty acids (i.e., having 5 or fewer carbon atoms in the chemical structure), medium-chain fatty acids (having 6-12 carbon atoms in the chemical structure), and other long chain fatty acids (i.e., having 13-21 carbon atoms in the chemical structure). Examples of saturated fatty acids include lauric acid ($CH_3(CH_2)_{10}COOH$), palmitic acid ($CH_3(CH_2)_{14}COOH$), stearic acid ($CH_3(CH_2)_{16}COOH$), and myristic acid ($CH_3(CH_2)_{12}COOH$). Oleic acid ($CH_3(CH_2)_7CH=CH(CH_2)_7COOH$) is an example of a naturally occurring unsaturated fatty acid. References may also be made to the salt or ester of a fatty acid, as well as its fatty amide moiety. For example, myristic acid may be referred to as myristate, and oleic acid may be referred to as oleate. A fatty acid moiety may also be a carboacyl of the fatty acid, i.e., a group formed by the loss of a hydroxide group of a carboxylic acid. In some embodiments, a fatty acid moiety may be bonded to a therapeutic agent through an amide bond. As an example, a myristic acid conjugate may have a fatty acid moiety $CH_3(CH_2)_{12}CO—NH—$, where the tertiary nitrogen s bonded to the therapeutic agent:

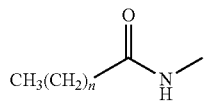

and n is an integer from to 20, and is preferably 10 to 20. This may result when the myristate moiety is conjugated through myristoylation, resulting in a tetradecanamide (or myristamide) group.

Numerous chemical spacer arms and linking group are known and available in the chemical arts. As used herein, "spacer arm" refers to a linear, branched, and/or cyclic moiety connecting a therapeutic agent to one of a linking group and a targeting signal moiety. There are numerous spacer arms known in the art, and the use of the term in this disclosure is preferably flexible, unless specified otherwise. The spacer arms can include substituted or unsubstituted $C_1$-$C_{20}$ alkyls and alkenyls. Demonstrative spacer arms include moieties selected from the group consisting of $—(CH_2)_m—$, $—(CH_2)_m—O—(CH_2)_m—$, $—(CH_2)_m—(NR_aR_b)(CH_2)_m—$, and combinations thereof. $R_a$ and $R_b$ in a given spacer arm can independently be hydrogen, alkyl, cycloalkyl, aryl, heterocycle, heteroaryl, or a combination thereof; or a nitrogen protecting group. In some embodiments, at least one of $R_a$ and $R_b$ may be absent. In some versions, the spacer arm can include moieties such as $(—(CH_2)_2—O)_m—(CH_2)_2—$. The subscript 'm' in any given spacer arm is a positive integer from 1 to 20.

As used herein, the term "linking group" refers to a moiety comprising a functional group capable of covalently reacting with (or reacted with) a functional group on another moiety, including a therapeutic agent, a spacer arm, and a targeting signal moiety. Example linking groups include substituted or unsubstituted $C_1$-$C_4$ alkenes, $—O—$, $—NR_c—$, $—OC(O)—$, $—S—$, $—S(O)_2—$, $—S(O)—$, $—C(O)NR_c—$, and $—S(O)_2NR_c—$, where c is an integer from 1 to 3.

The phrase "anti-aging" is meant to broadly reference and include inhibiting and/or killing senescent cells, delaying the development of senescent cells, preventing acquisition of a senescence-associated secretory phenotype, facilitating tissue repair and regeneration, increasing at least one of organismal life-span and health-span, and delaying the onset of age-related illnesses and effects. Of course, aging causes numerous unwanted effects. The present approach may reduce one or more of hair loss, hearing loss, vision loss, memory loss, mental slowness, joint stiffness, muscle loss, strength loss, speed loss, balance loss, endurance loss, agility loss, sexual dysfunction, virility loss, testosterone reduction, lipofuscin deposits, and inflammation. The present approach may improve and/or increase one or more of hair regeneration, hearing, vision, memory, mental acuity, joint mobility, muscle growth, muscular strength, muscular endurance, speed, balance, agility, and sexual performance. For example, the present approach has the potential to restore hair growth and natural hair color, restore muscular coordination and gait, restore overall mobility, increase muscle mass, increase grip strength, increase concentration ability and mental clarity, increase learning and memory, and result in an overall feeling of well-being and positive energy in mammals that would otherwise suffer from aging side-effects. Embodiments of the present approach have demonstrated a reduction in gray hair, overall frailty, forgetfulness, and general aches and pains.

The mitochondria is an untapped gateway for treating a number of afflictions, ranging from cancer to bacterial and fungal infections to aging. Functional mitochondria are required for the propagation of cells that are related to aging, such as senescent cells, cells having accumulated DNA damage and/or oxidative damage, and cancer stem cells. Inhibiting mitochondrial biogenesis and metabolism in these cells impedes the propagation of those cells, and reduces the accumulated DNA and oxidative damage. Mitochondrial inhibitors therefore represent a new class of anti-aging and anti-cancer therapeutics.

The inventors analyzed phenotypic properties of CSCs that could be targeted across a wide range of cancer types, and identified a strict dependence of CSCs on mitochondrial biogenesis for the clonal expansion and survival of a CSC. This strategy of attacking cellular metabolism may also be used to target senescent cells under the present approach. Previous work by the inventors demonstrated that different classes of FDA-approved antibiotics, and in particular tetracyclines such as doxycycline and erythromycin, have an off-target effect of inhibiting mitochondrial biogenesis. As a result, such compounds have efficacy for eradicating CSCs and senescent cells. However, these common antibiotics were not designed to target the mitochondria, leaving considerable room for improving their anti-cancer efficacy. Similarly, modern medicine has considered these off-target effects to be undesirable. Under the present approach, existing antibiotics having intrinsic anti-mitochondrial properties may be used in connection with one or more pro-oxidants, to inhibit mitochondrial biogenesis and metabolism in CSCs and senescent cells under mitochondrial oxidative stress. In some embodiments, one or more therapeutic agents may be chemically modified with a membrane-targeting signal or a mitochondria-targeting signal to further increase the therapeutic agent's uptake at CSC or senescent cell mitochondria. Mitochondria-targeting signals may significantly increase this targeted uptake, often by 100s of times, if not more.

Doxycycline impacts cancer growth through inhibition of CSC propagation with an IC-50 between 2-to-10 μM. The Antibiotic for Breast Cancer (ABC) trial was conducted at The University of Pisa Hospital. The ABC trial aimed to assess the anti-proliferative and anti-CSC mechanistic actions of doxycycline in early breast cancer patients. The primary endpoint of the ABC trial was to determine whether short-term (e.g., 2 weeks) pre-operative treatment with oral doxycycline of stage I-to-III early breast cancer patients resulted in inhibition of tumor proliferation markers, as determined by a reduction in tumor Ki67 from baseline (pre-treatment) to post-treatment, at the time of surgical excision. Secondary endpoints were used to determine if pre-operative treatment with doxycycline in the same breast cancer patients resulted in inhibition of CSC propagation and a reduction of mitochondrial markers.

A pilot study of the ABC trial confirmed that doxycycline treatment successfully decreases the expression of CSC markers in breast cancer tumor samples. Post-doxycycline tumor samples demonstrated a statistically significant 40% decrease in the stemness marker CD44, when compared to pre-doxycycline tumor samples. CD44 levels were reduced between 17.65% and 66.67%, in 8 out of 9 patients treated with doxycycline. In contrast, only one patient showed a rise in CD44, by 15%. This represents a 90% positive response rate. Similar results were also obtained with ALDH1, another marker of stemness, especially in HER2(+) patients. In contrast, markers of mitochondria, proliferation, apoptosis and neo-angiogenesis, were all similar between the two groups. These results suggest that doxycycline can selectively eradicate CSCs in breast cancer patients in vivo.

The present approach expands on the ABC trial, through amplifying the impact of doxycycline, with a second anti-mitochondrial biogenesis therapeutic agent that targets the large mitochondrial ribosome, and a pro-oxidant that induces mitochondrial oxidative stress in CSCs and senescent cells. Embodiments of the present approach significantly enhance the CSC propagation inhibitory effects of antibiotics that inhibit mitochondrial biogenesis, such as doxycycline, through a triple combination therapy having at least one antibiotic that inhibits the large mitochondrial ribosome, at least one antibiotic that inhibits the small mitochondrial ribosome, and at least one pro-oxidant. In demonstrative embodiments discussed below, the therapeutic agents include azithromycin, doxycycline, and Vitamin C. It should be appreciated that other mitochondrial biogenesis inhibitors and sources of mitochondrial oxidative stress may be used.

Figure 1B:
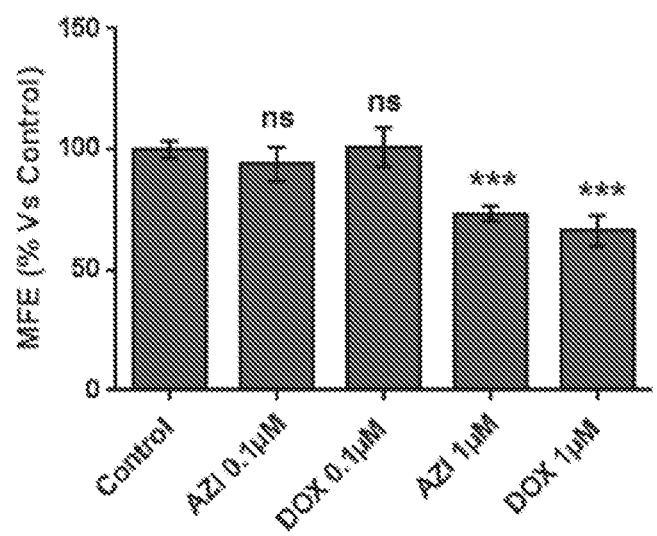
Figure 1C:
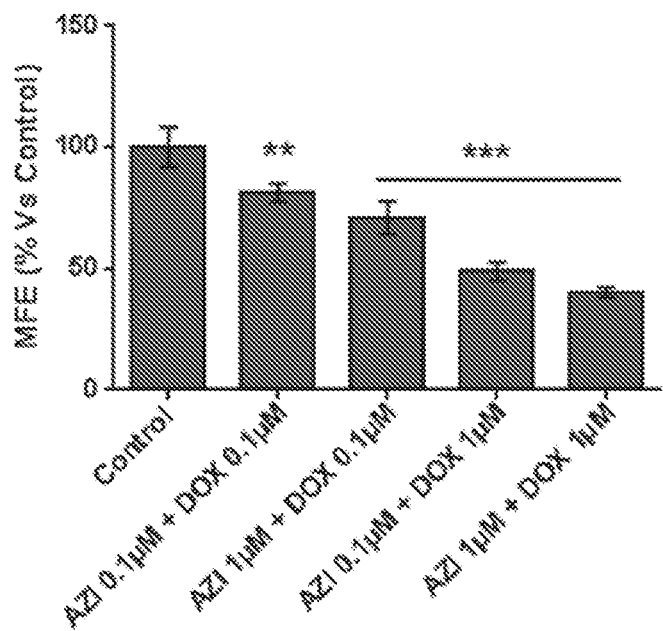

The following paragraphs discuss laboratory data and analysis for select embodiments of the present approach. Doxycycline and azithromycin were tested alone and in combination at low concentrations to evaluate the resulting inhibitory effect on mammosphere formation. FIGS. 1A-1C summarize mammosphere formation data for varying concentrations and combinations. In particular, FIG. 1A shows mammosphere formation assay results for azithromycin, at concentrations from 0.1 μM to 100 μM. FIG. 1B compares mammosphere formation assay results for comparable concentrations of azithromycin ("azi") and doxycycline ("dox"). FIG. 1C shows the combined effects of azithromycin and doxycycline in the mammosphere formation assay. As can be seen, doxycycline and azithromycin alone at low concentrations (0.1 μM and 1 μM) had little or no effect on the inhibition of mammosphere formation. However, FIG. 1C shows that the combination of 1 μM doxycycline and 1 μM azithromycin exerted a very significant inhibitory effect on mammosphere formation.

The combination of doxycycline and azithromycin has a marked increased efficacy in the inhibition of mammosphere formation, relative to when the drugs are used alone. For example, the IC-50 for the combination is about 50-fold lower than for azithromycin alone and 2-to-5 fold lower than for doxycycline alone. These results demonstrate that a combination of doxycycline and azithromycin have more therapeutic efficacy than either therapeutic agent used alone.

Figure 2A:
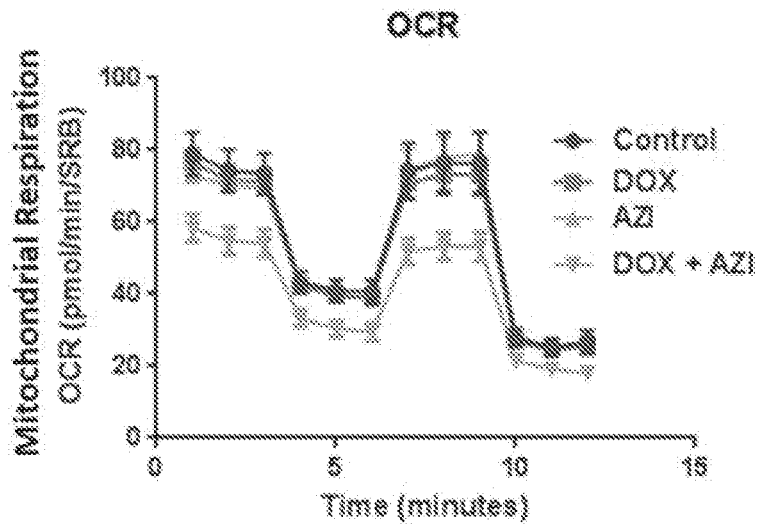
FIGS. 2A-2D summarize metabolic profile data for MCF7 cells pre-treated with doxycycline, azithromycin, and the combination of doxycycline and azithromycin, at concentrations of 1 µM.
Figure 2B:
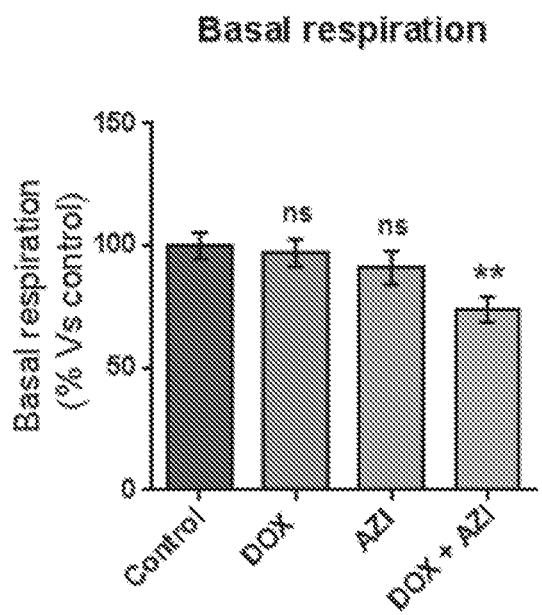
Figure 2C:
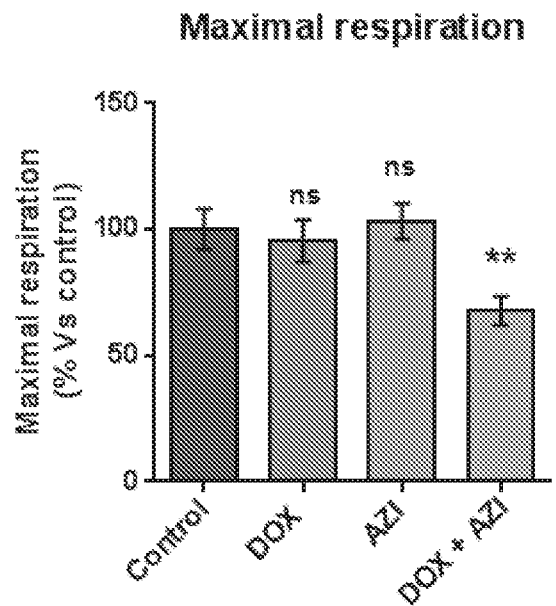
Figure 2D:
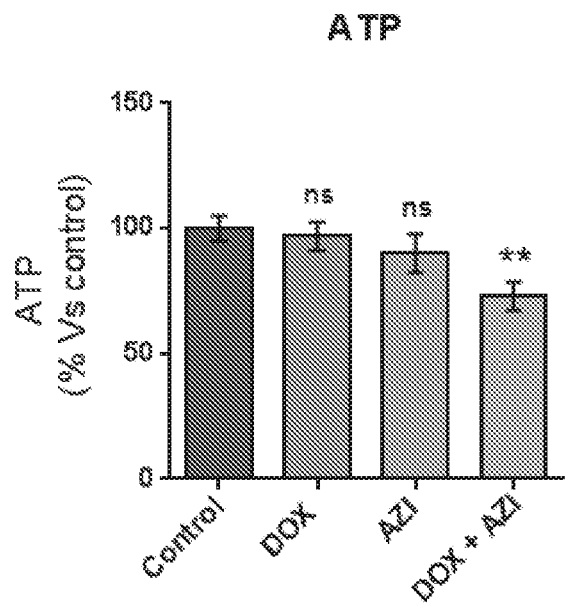
Figure 3A:
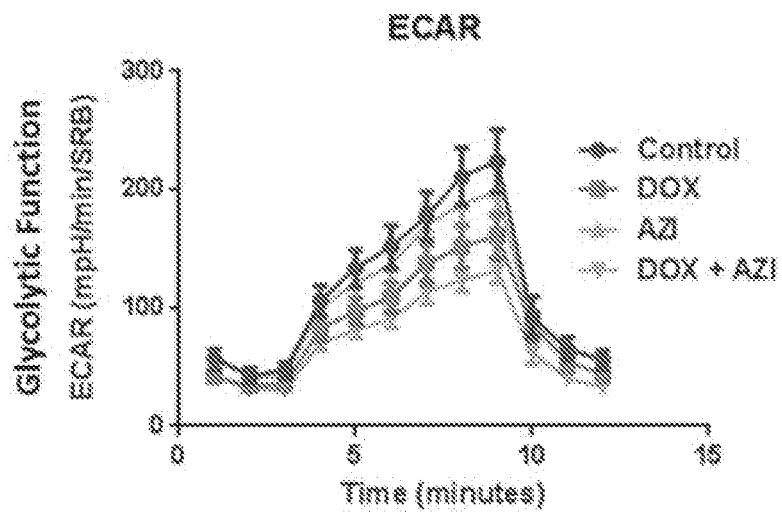
FIGS. 3A-3D summarize extracellular acidification rate (ECAR), glycolysis, glycolytic reserve, and glycolytic reserve capacity data, respectively, for MCF7 cells pre-treated with doxycycline, azithromycin, and the combination of doxycycline and azithromycin, at concentrations of 1 µM.
Figure 3B:
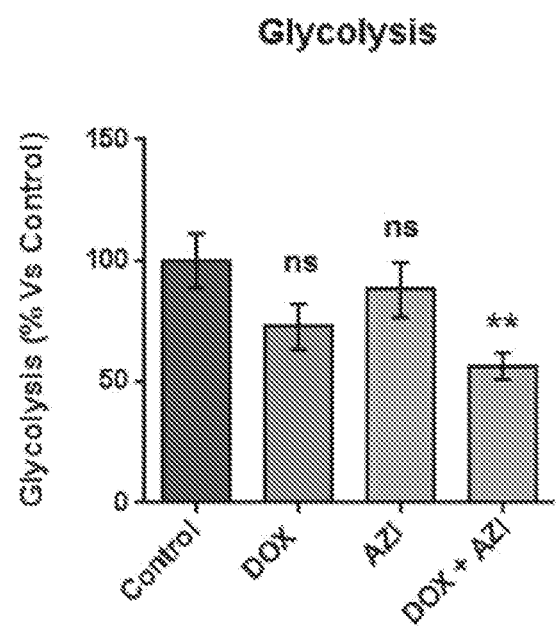
Figure 3C:
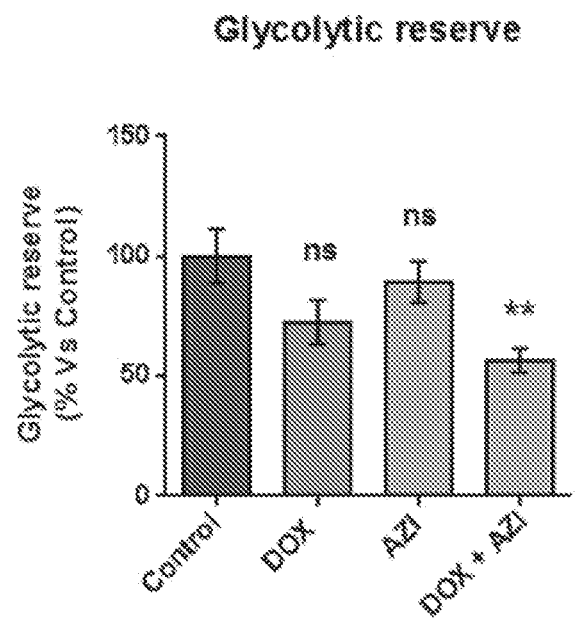
Figure 3D:
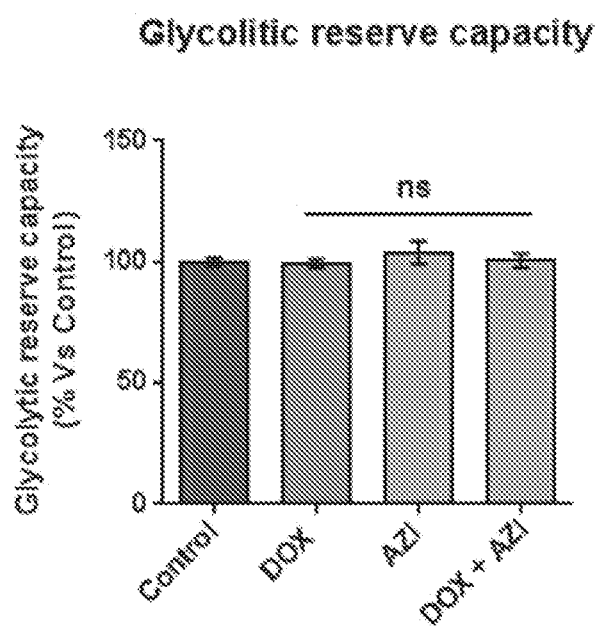
Figure 4A:
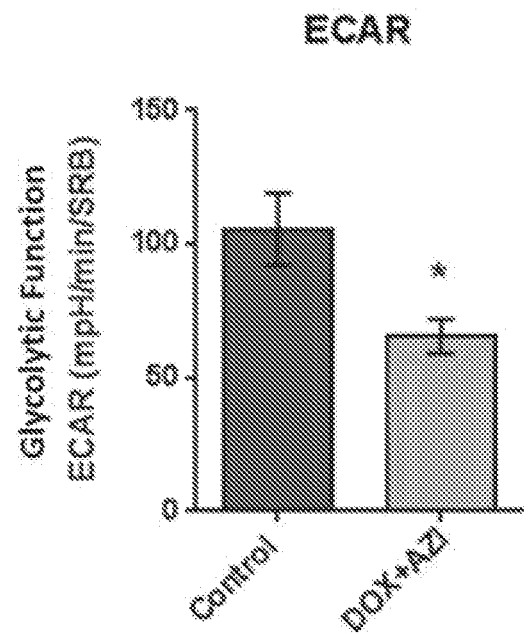
FIG. 4A compares ECAR data for the combination of 1 µM doxycycline and 1 µM azithromycin against the control, and FIG. 4B compares OCR and ECAR ratios of the combination to the control.
Figure 4B:
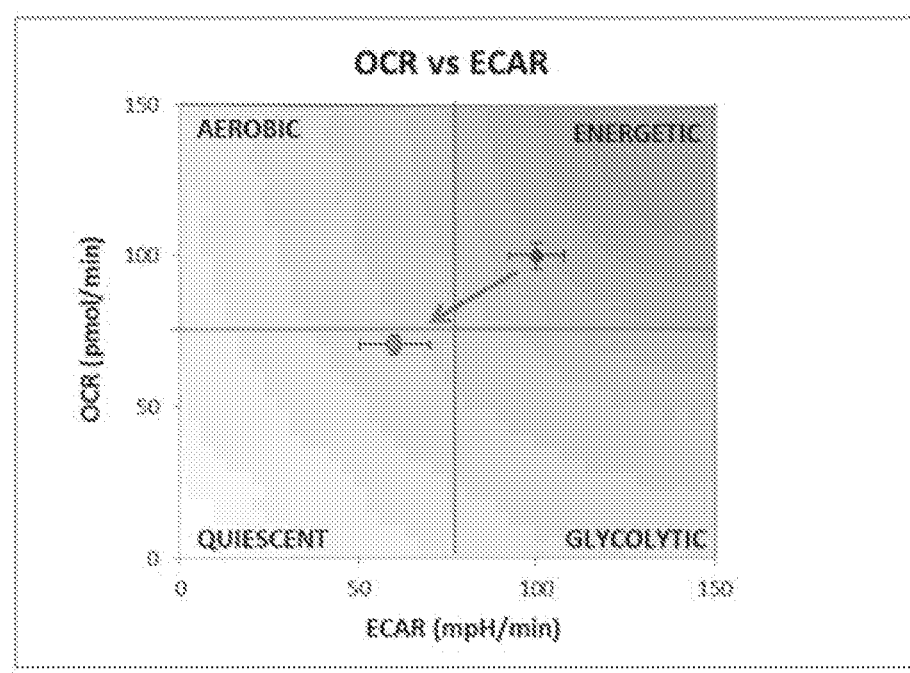

The combination's inhibitory effects on mammosphere formation relate to mitochondrial function. The metabolic profile of MCF7 cell monolayers pre-treated with the combination of 1 μM doxycycline and 1 μM azithromycin, or with the same drugs alone, for 3-days were examined to confirm this relationship. FIGS. 2A-2D summarize metabolic profile data for MCF7 cells pre-treated with doxycycline, azithromycin, and the combination of doxycycline and azithromycin, at concentrations of 1 μM. FIG. 2A shows oxygen consumption rate over time, and FIGS. 2B-2D show basal respiration, maximal respiration, and ATP production, respectively. Interestingly, the rates of both oxidative mitochondrial metabolism and glycolysis were significantly reduced by the combination pre-treatment, as assessed using the Seahorse XFe96 analyzer. This resulted in significant reductions in respiration (basal and maximal), as well as reduced ATP levels. FIGS. 3A-3D summarize extracellular acidification rate (ECAR), glycolysis, glycolytic reserve, and glycolytic reserve capacity data, respectively, for MCF7 cells pre-treated with doxycycline, azithromycin, and the combination of doxycycline and azithromycin, at concentrations of 1 μM. Both glycolysis and glycolytic reserve were decreased by the combination of doxycycline and azithromycin. This reduction is understood to be an acute effect of treatment with mitochondrial biogenesis inhibitors. Over time, the surviving CSC or senescent cell population would be expected to have a glycolytic metabolic profile. FIG. 4A compares ECAR of the combination against the control, and FIG. 4B compares OCR and ECAR ratios of the combination to the control. The data in FIGS. 4A and 4B show that MCF7 cancer cells shifted from a highly energetic profile to a metabolically quiescent state following the combination treatment.

Figure 5:
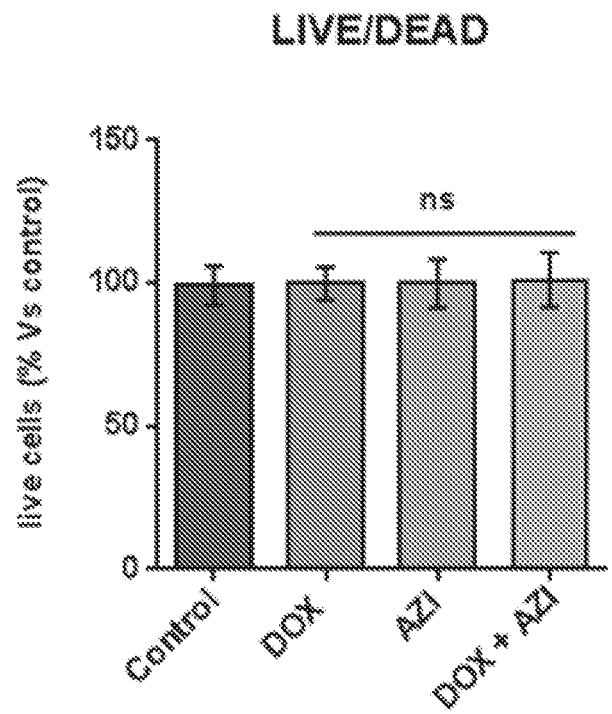
FIG. 5 summarizes toxicity data for normal cells treated with doxycycline, azithromycin, and the combination of doxycycline and azithromycin.

With respect to toxicity, embodiments of the present approach are non-toxic towards normal, healthy cells. FIG. 5 summarizes demonstrative toxicity data, in the form of the percentage of living cells remaining under anchorage-independent growth conditions, in samples treated with 1 μM of doxycycline, 1 μM of azithromycin, and the combination of 1 μM of doxycycline and 1 μM of azithromycin. Following monolayer treatment with either doxycycline alone, azithromycin alone, or the combination, for 48 hours, the CSC population was enriched by seeding onto low-attachment plates. Under these conditions, the non-CSC population undergoes anoikis (a form of apoptosis induced by a lack of cell-substrate attachment) and CSCs are believed to survive. The surviving CSC fraction was then determined by FACS analysis. Briefly, 1×104 MCF7 monolayer cells were treated with antibiotics or vehicle alone for 48 h in 6-well plates. Then, cells were trypsinized and seeded in low-attachment plates in mammosphere media. After 12 h, the MCF7 cells were spun down. Cells were rinsed twice and incubated with LIVE/DEAD dye (Fixable Dead Violet reactive dye; Invitrogen) for 10 minutes. Samples were then analyzed by FACS (Fortessa, BD Bioscence). The live population was then identified by employing the LIVE/DEAD dye staining assay as is known in the art. Data were analyzed using FlowJo software. FIG. 5 shows minimal cell death for the therapeutic agents tested. As can be seen, the combination of 1 µM Doxycycline with 1 µM Azithromycin is non-toxic under anchorage-independent growth conditions. Taken together, the experimental results show that the combination of doxycycline and azithromycin, particularly at low doses, are more effective than doxycycline alone, for CSC eradication.

Compounds described herein have demonstrated potent senolytic behavior in senescent MRC-5 cells. Bromodeoxyuridine (5-bromo-2'-deoxyuridine), also known as BrdU, was used to induce senescence. BrdU is an analog of the nucleoside thymidine commonly used to identify proliferating cells. BrdU induces controlled DNA damage, and drives cells towards senescence with high efficiency. The BrdU assay of the present approach calls for subjecting normal fibroblasts to prolonged culture (8-days) in the presence of BrdU at 100 µM to induce controlled DNA-damage and senescence. In demonstrative embodiments, the inventors used two independent normal, non-immortalized, human fibroblast cell lines, MRC-5 lung cells (for screening) and BJ skin cells (for validation), in the BrdU-based assay. Then, isogenically-matched cultures of normal and senescent fibroblasts may be used for drug screening to identify drugs having senolytic activity. Senolytic activity may be detected using the sulforhodamine B assay, also known in the art as the SRB assay. This assay measures the amount of protein remaining attached to the tissue-culture dishes, and is a surrogate marker for cell viability. This approach may be used to rapidly screen compounds, including clinically-approved drugs, such as, for example, antibiotics. For example, in embodiments described herein, the present approach was used to screen erythromycin family members, including azithromycin and roxithromycin, among other compounds and conjugates. It should be appreciated that the present approach may be used to screen other compounds.

Figure 19:
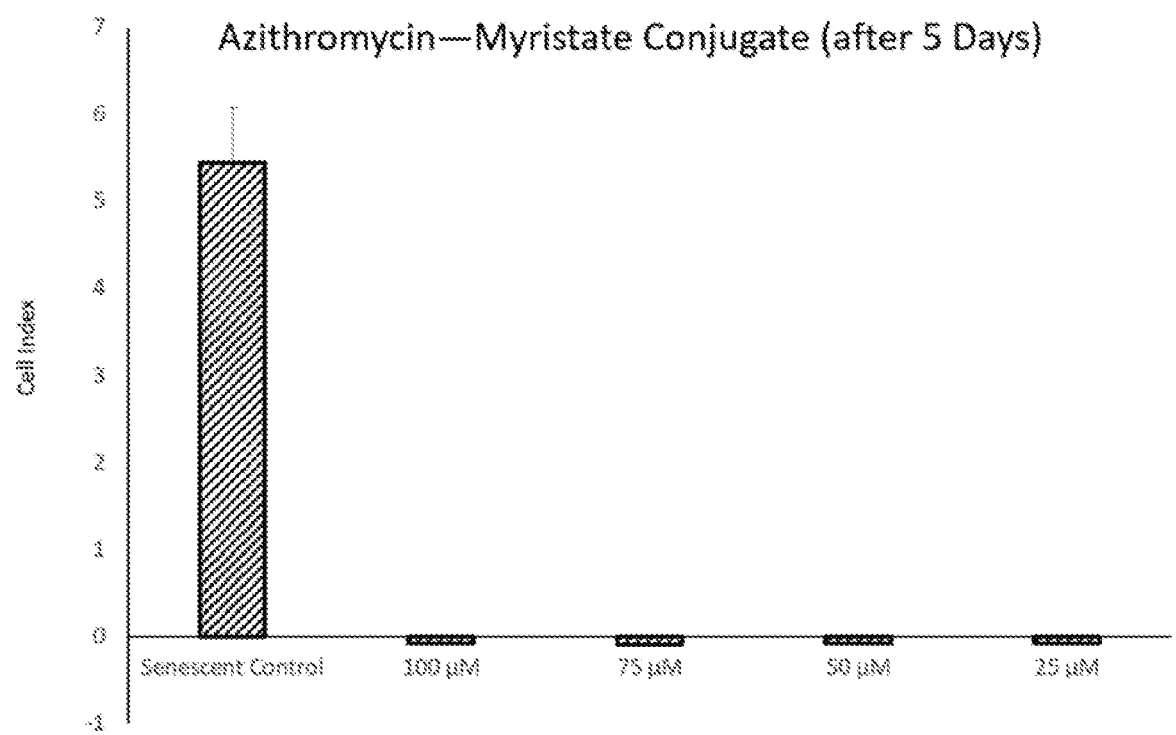
FIG. 19 shows final cell index results and a representative cell tracing from xCELLigence real-time cell health monitoring, for MRC-5 cell lines comparing BrdU pretreatment alone to BrdU pretreatment with an azithromycin—fatty acid conjugate at various concentrations.

FIG. 19 shows representative data from xCELLigence assays for azithromycin conjugated with myristate at various concentrations. The data in FIG. 19 highlights the final cell index after 5 days, and shows that senescent cells (BrdU-treated MRC-5 fibroblasts) were effectively killed by the conjugate. As can be seen, the azithromycin—fatty acid conjugate targeted nearly 100% of the senescent MRC-5 cells, even at concentrations as low as 25 µM.

Figure 6A:
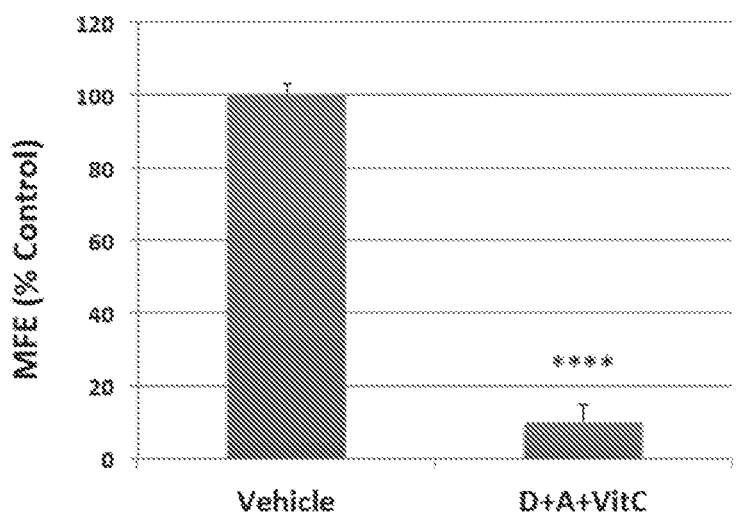
FIG. 6 summarizes mammosphere formation after simultaneous treatment according to one embodiment of the present approach.
Figure 6B:
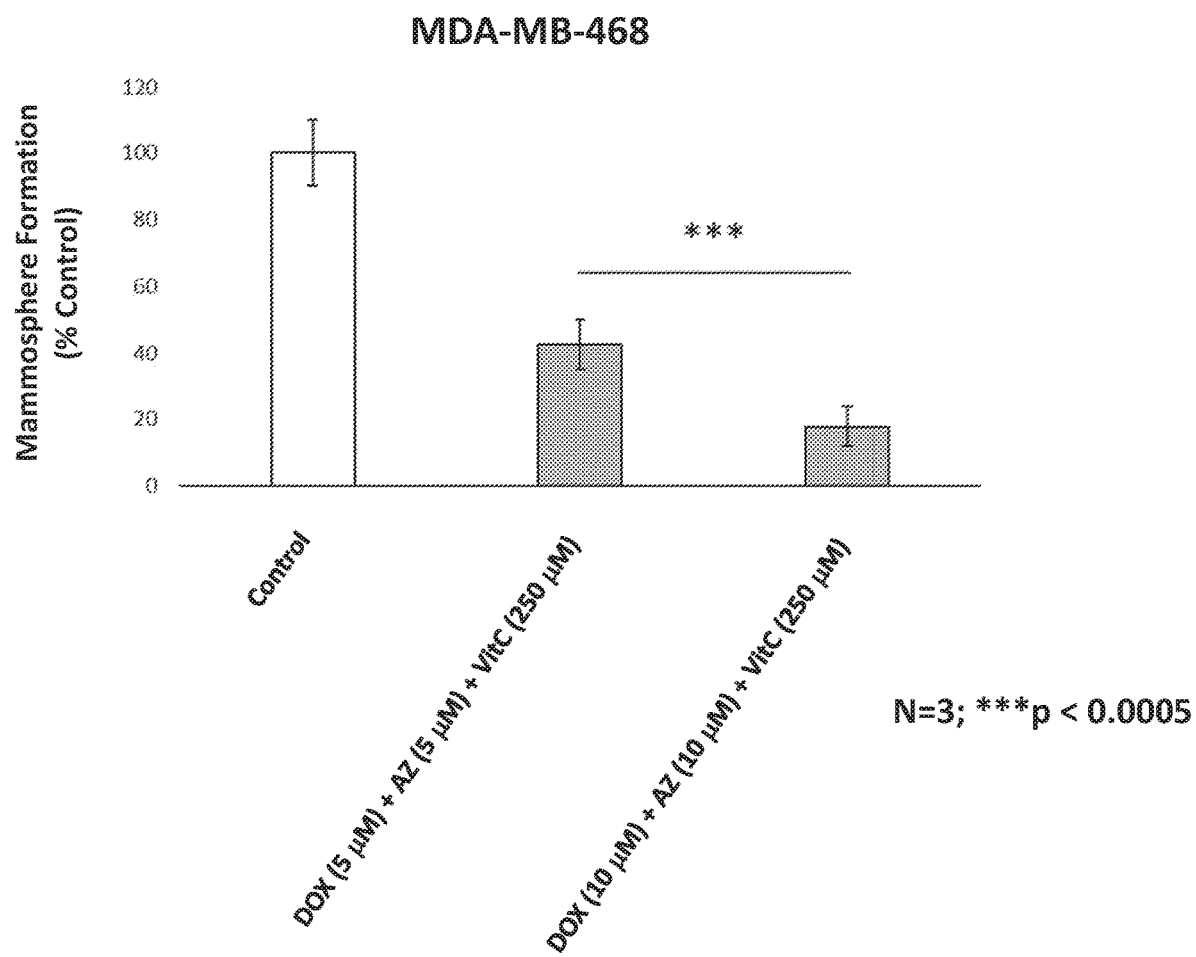

Introducing a pro-oxidant to the combination provides an even stronger anti-cancer and anti-aging effect to the combination of doxycycline and azithromycin, and the conjugated compounds described herein. However, the present approach is not limited to the use of azithromycin, doxycycline, and Vitamin C. A variety of experimental results confirm that the triple combination of a first antibiotic inhibiting the large mitochondrial ribosome, and a second antibiotic inhibiting the small mitochondrial ribosome, and a pro-oxidant, has potent anti-cancer and anti-aging properties. The combination of three therapeutic agents is significantly more effective than any of them individually or in pairs, with respect to anti-cancer activity. In demonstrative examples, an embodiment having a combination of doxycycline, azithromycin, and Vitamin C has been confirmed to effectively inhibit CSC and senescent cell propagation. FIG. 6A summarizes mammosphere formation in MCF7 cells after simultaneous treatment with a composition having 1 µM doxycycline, 1 µM azithromycin, and 250 µM Vitamin C. FIG. 6B compares mammosphere formation in MDA-MB-468 cells (a triple-negative human breast cancer cell line) after simultaneous treatment with, in one data set, a first composition having 5 µM doxycycline, 5 µM azithromycin, and 250 µM Vitamin C, and in another data set, a second composition having 10 µM doxycycline, 10 µM azithromycin, and 250 µM Vitamin C. The data demonstrates that the triple combination embodiments of the present approach inhibited CSC propagation by as much as ~90%, compared to the control. Thus, near complete ablation of 3D tumor-sphere forming abilities was achieved at very low therapeutic agent concentrations, demonstrating that CSCs are vulnerable to embodiments of the present approach. It should be appreciated that the therapeutic agent concentrations described herein are demonstrative, and that other concentrations of therapeutic agents may be pharmaceutically effective. Advantageously, embodiments of the present approach remain effective even at sub-microbial concentrations of the antibiotics.

Figure 7A:
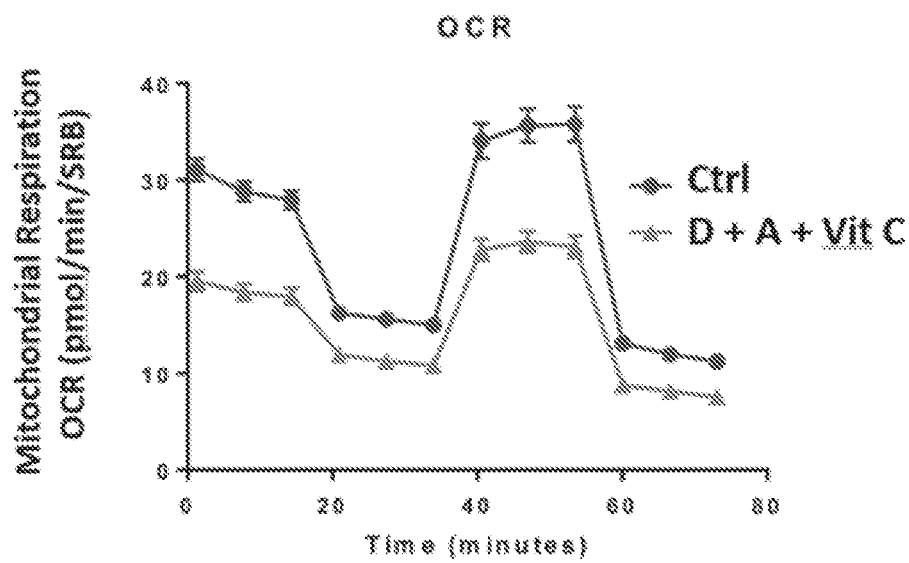
FIGS. 7A and 7B are Seahorse profiles showing inhibition of oxidative mitochondrial metabolism (FIG. 7A) and glycolytic function (FIG. 7B) by an embodiment of the present approach.
Figure 7B:
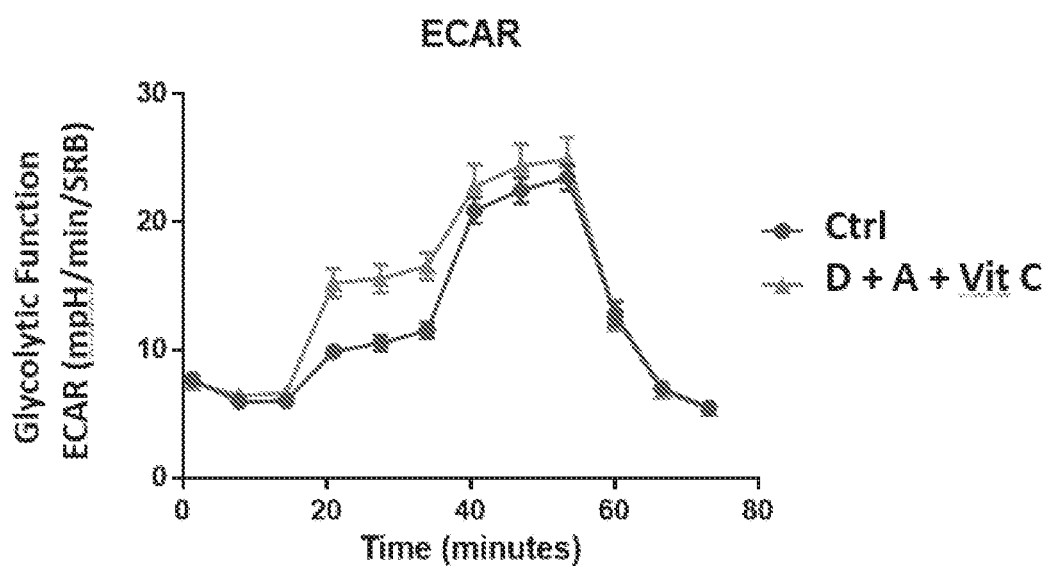
Figure 8A:
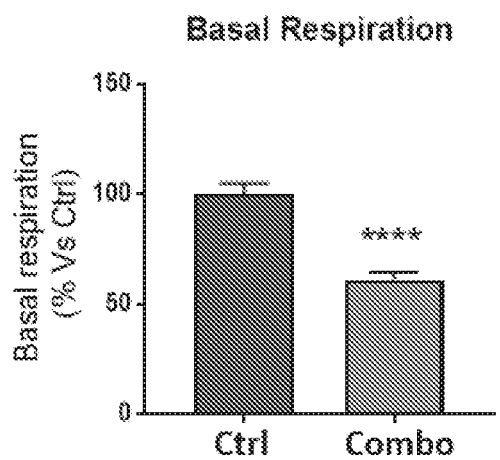
FIGS. 8A-8F show metabolic profile data for MCF7 cells pre-treated according to one embodiment of the present approach.
Figure 8B:
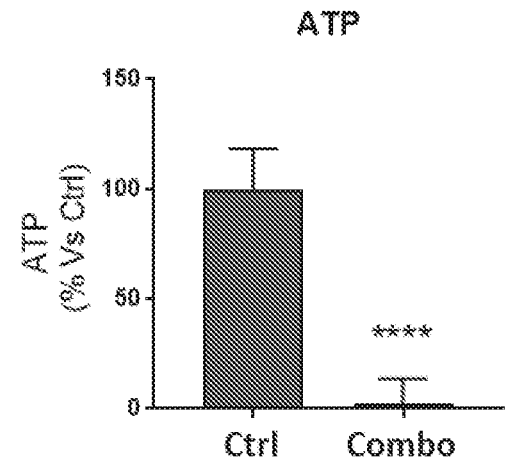
Figure 8C:
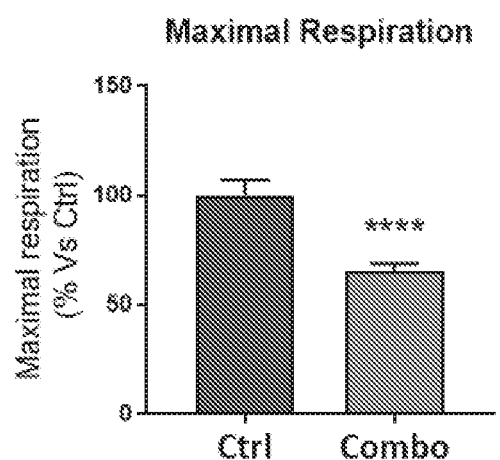
Figure 8D:
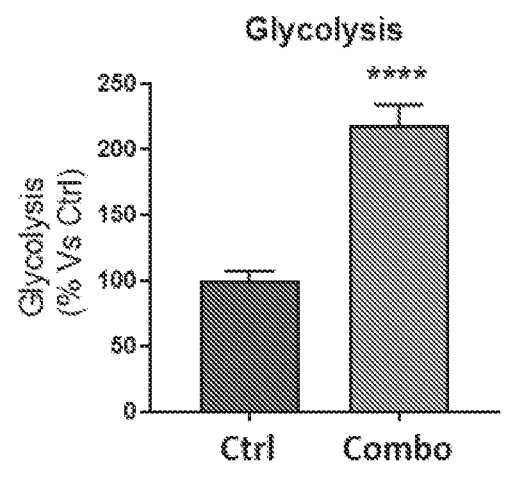
Figure 8E:
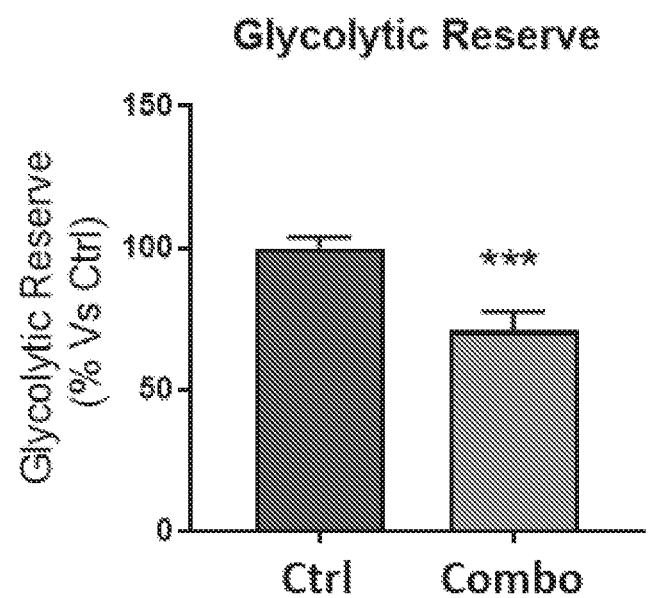
Figure 8F:
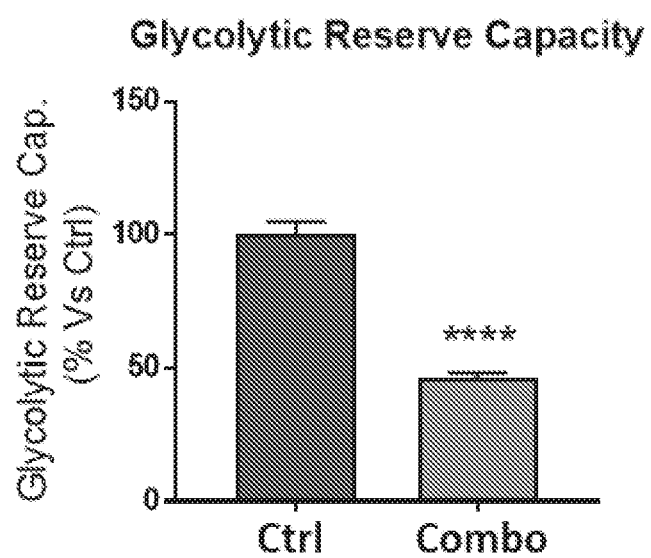

Additional data confirms the inhibitory effects of the triple combination of a first antibiotic inhibiting the large mitochondrial ribosome, and a second antibiotic inhibiting the small mitochondrial ribosome, and pro-oxidant, on CSC mitochondrial function. FIGS. 7A-7B and 8A-8F show metabolic profiles, including oxygen consumption rate over time, basal respiration, maximal respiration, ATP production, and spare respiratory capacity, respectively, for MCF7 cell monolayers pre-treated with a combination of 1 µM doxycycline, 1 µM azithromycin, and 250 µM Vitamin C for 3-days. FIGS. 7A and 7B are Seahorse profiles showing inhibition of oxidative mitochondrial metabolism (FIG. 7A) and glycolytic function (FIG. 7B) by an embodiment of the present approach. As can be seen, the triple combination inhibited oxidative mitochondrial metabolism (measured by OCR) and induced glycolytic function (measured by ECAR). FIGS. 8A-8F summarize metabolic data for MCF7 cells pre-treated with doxycycline, azithromycin, and the combination of doxycycline and azithromycin, at concentrations of 1 µM and 250 µM Vitamin C. The rates of both oxidative mitochondrial metabolism and glycolysis were significantly reduced by the combination pre-treatment, as assessed using the Seahorse XFe96 analyzer. Remarkably, the rate of oxidative mitochondrial metabolism was reduced by over 50% and ATP levels were drastically reduced, as assessed using the Seahorse XFe96 analyzer. Overall, this resulted in significant reductions in both basal and maximal respiration. In contrast, glycolysis was increased, but glycolytic reserve was decreased, in the cell monolayers pre-treated with the triple combination embodiment tested.

Figure 9A:
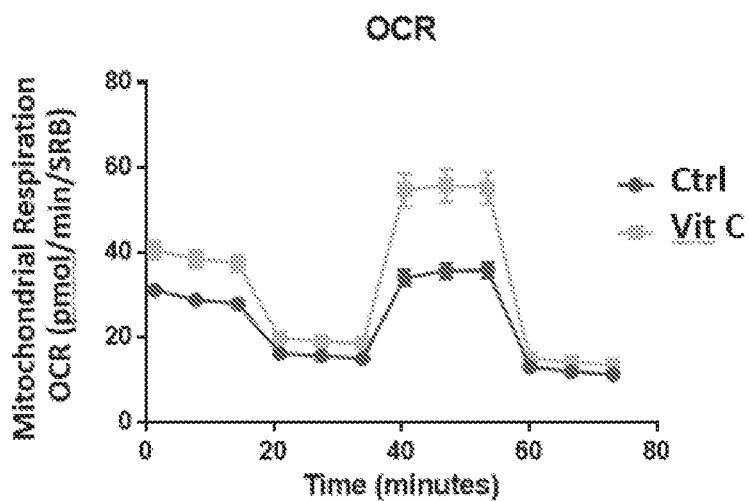
FIGS. 9A and 9B summarize Seahorse profiles (OCR and ECAR data, respectively) for MCF7 cells treated with 250 µM Vitamin C, alone, compared to a control.
Figure 9B:
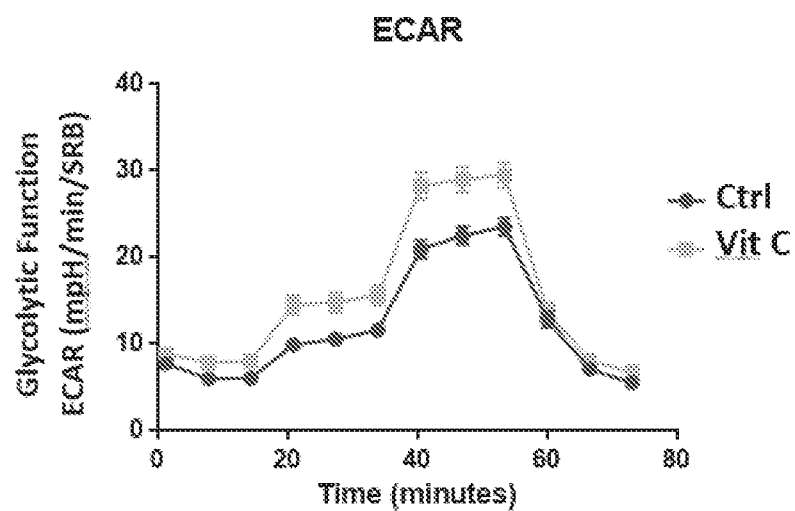
Figure 10A:
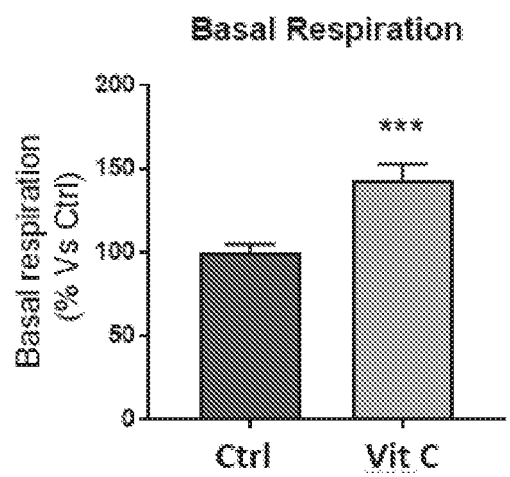
FIGS. 10A-10F show metabolic profile data for MCF7 cells pre-treated with 250 µM Vitamin C for three days.
Figure 10B:
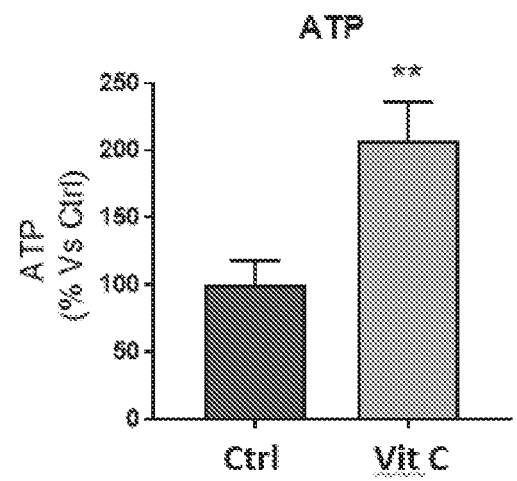
Figure 10C:
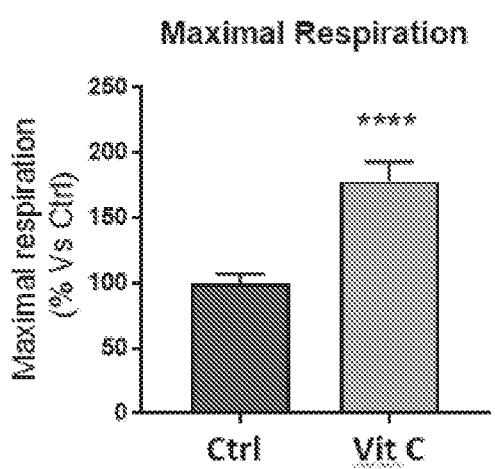
Figure 10D:
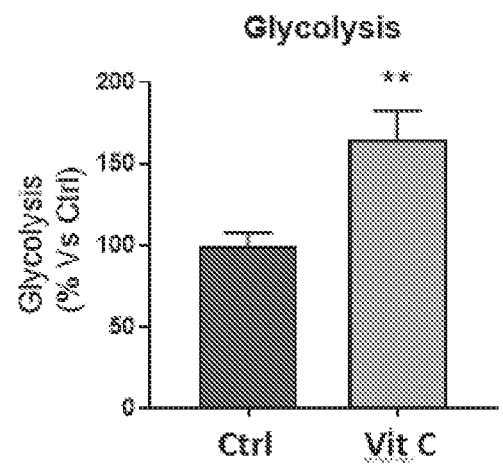
Figure 10E:
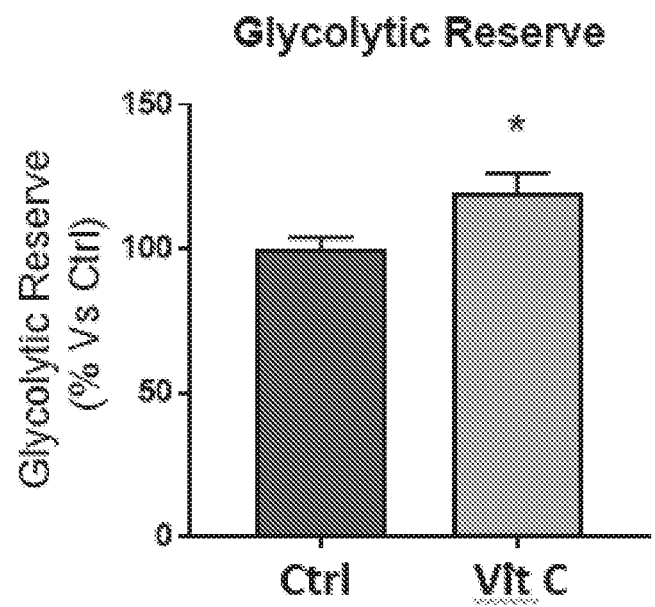
Figure 10F:
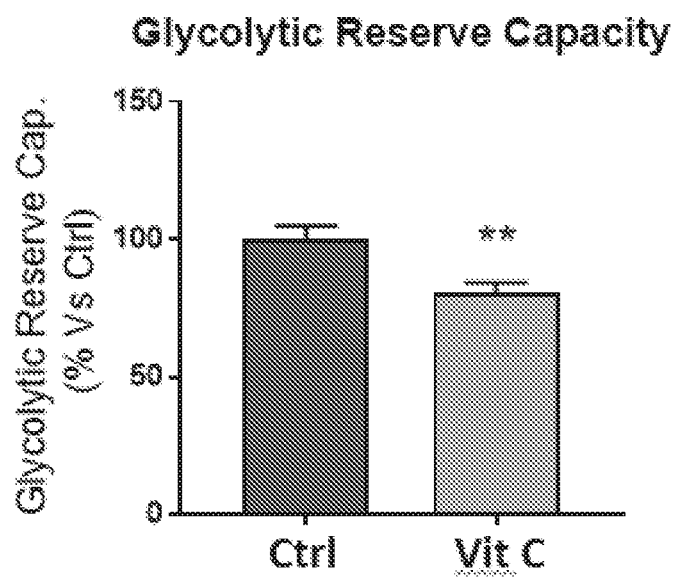

Inclusion of a pro-oxidant has an unexpected yet valuable effect on embodiments of the present approach. FIGS. 9A and 9B summarize OCR and ECAR data for MCF7 cells treated with 250 µM Vitamin C, alone, compared to a control. As seen in the data, treatment with 250 µM Vitamin C (alone) significantly increased both mitochondrial metabolism and glycolysis in MCF7 cancer cells. FIGS. 10A-10F show metabolic profile data for MCF7 cells pre-treated with 250 µM Vitamin C for three days. Treatment with 250 µM Vitamin C significantly increased basal respiration, ATP production and maximal respiration. Treatment with 250 µM Vitamin C significantly increased glycolysis and glycolytic reserves, while decreasing glycolytic reserve capacity. These observations indicate that Vitamin C alone acts as a mild pro-oxidant, and through mitochondrial oxidative stress the therapeutic agent stimulates mitochondrial biogenesis in cancer cells, driving increased mitochondrial metabolism (e.g., increased mitochondrial protein synthesis and ATP production). Nuclear mitochondrial protein and mt-DNA encoded protein production is increased in the cell. This interpretation is consistent with the experimental data directly showing that embodiments having one or more antibiotics inhibiting the large mitochondrial ribosome and one or more antibiotics inhibiting the small mitochondrial ribosome, and a pro-oxidant, effectively eradicate cancer cells. In particular, the mitochondrial biogenesis inhibitors prevent the increased mitochondrial metabolism induced by Vitamin C. The combination inhibits the synthesis of proteins encoded by the mitochondrial DNA (mt-DNA), leading to a depletion of essential protein components essential for OXPHOS in the CSCs. Without these proteins, the CSCs and senescent cells experience abnormal mitochondrial biogenesis and severe ATP depletion.

Figure 11A:
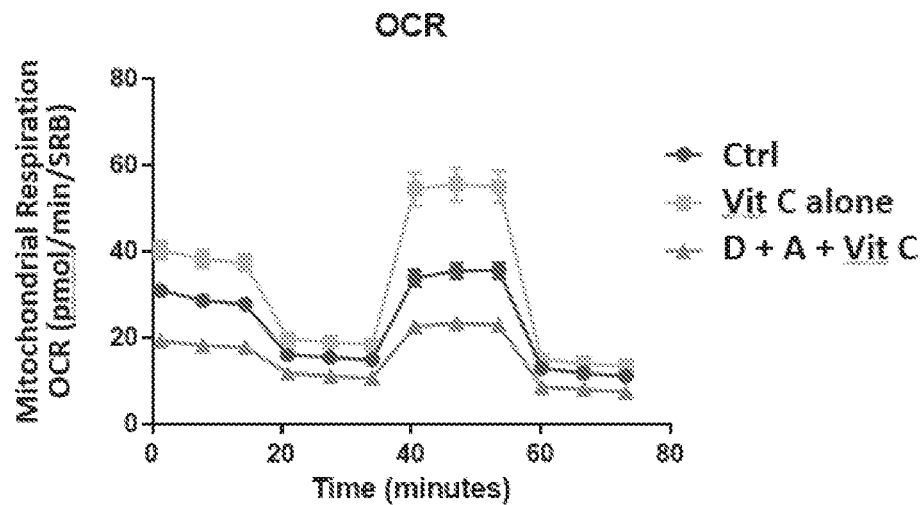
FIGS. 11A and 11B show Seahorse profiles (OCR and ECAR data, respectively) for low-dose Vitamin C and a triple combination of therapeutic agents according to an embodiment of the present approach.
Figure 11B:
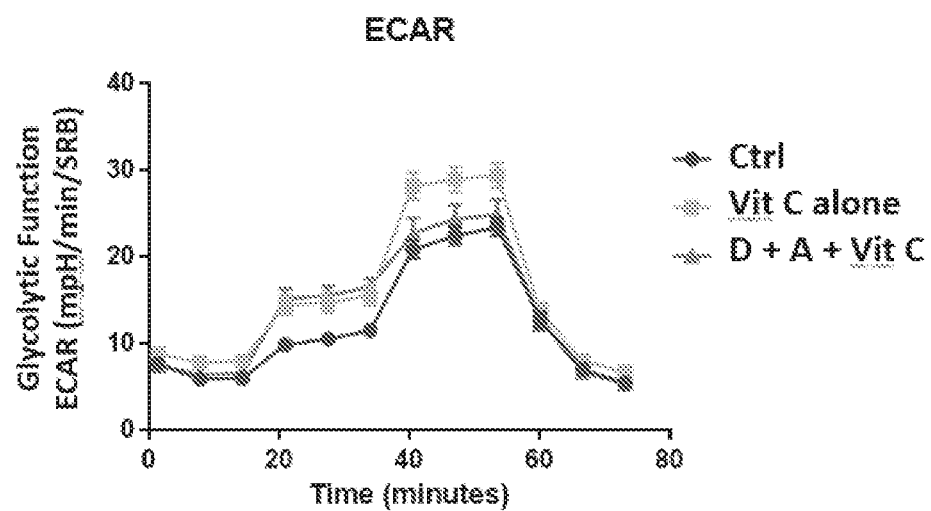
Figure 12A:
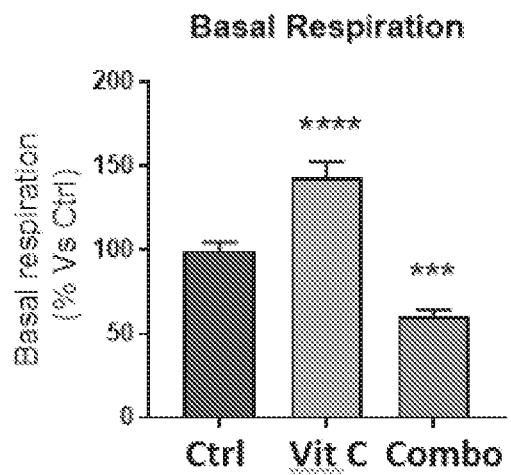
FIGS. 12A-12F show side-by-side metabolic profile data, comparing low-dose Vitamin C with an embodiment of the triple combination according to the present approach.
Figure 12B:
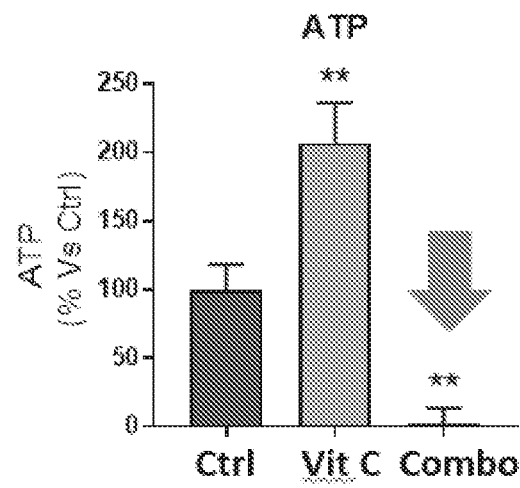
Figure 12C:
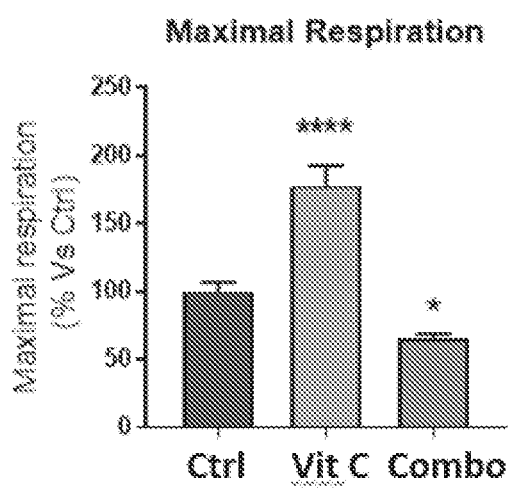
Figure 12D:
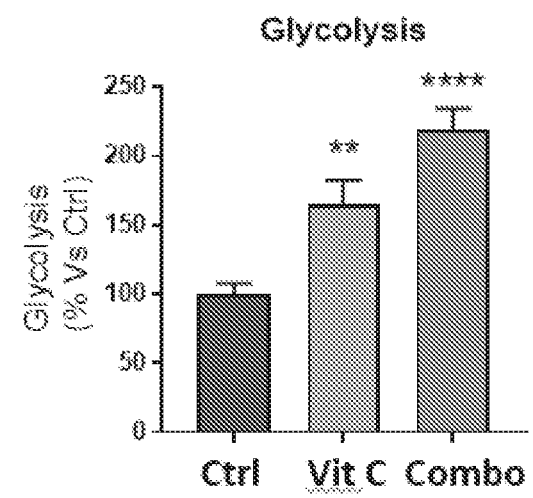
Figure 12E:
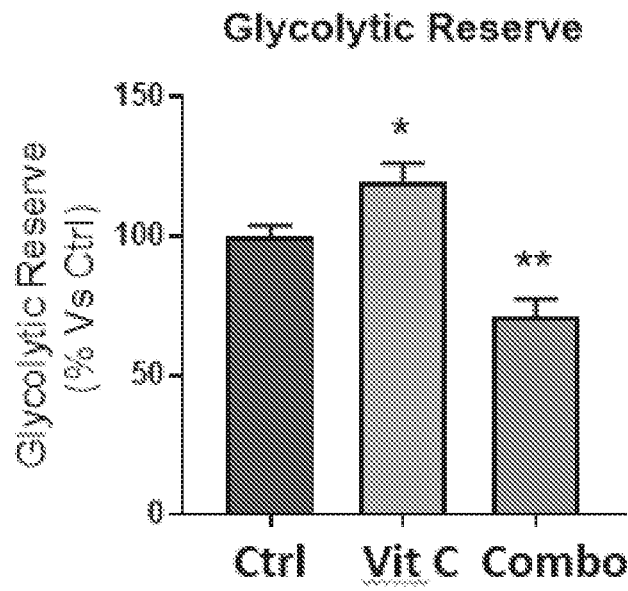
Figure 12F:
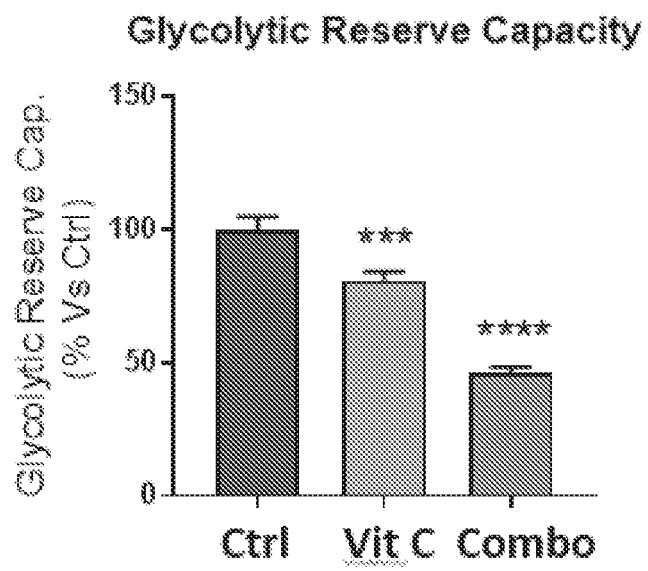

FIGS. 11A and 11B show Seahorse profiles (OCR and ECAR data, respectively) for low-dose Vitamin C and a triple combination according to an embodiment of the present approach. These side-by-side metabolic comparisons show that low-dose Vitamin C increases oxidative mitochondrial metabolism, whereas the triple combination resulted in severe ATP depletion. Low-dose Vitamin C (e.g., sufficient to achieve a peak Vitamin C concentration in at least one of the blood, serum, and plasma, of about 500 µM or less) and the triple combination both increased glycolysis. FIGS. 12A-12F show the metabolic data for the comparison in FIGS. 11A and 11B. Low-dose Vitamin C increased basal respiration, ATP production and maximal respiration, whereas the triple combination decreased all three of these parameters. Also, low-dose Vitamin C and the triple combination both increased glycolysis, while decreasing glycolytic reserve capacity. These results show that inclusion of two mitochondrial biogenesis inhibitors, one inhibiting the large mitochondrial ribosome and the second inhibiting the small mitochondrial ribosome, with Vitamin C, blocks and reverses the Vitamin C induced increase in mitochondrial oxidative metabolism. The combination of all three therapeutic agents results in significantly improved anti-cancer and anti-aging activity. In some embodiments of the present approach, Vitamin C (which includes ascorbate derivatives that may behave as reducing agents) may be replaced with another agent that induces mitochondrial oxidative stress, such as certain chemotherapeutics and radiation treatment.

The temporal effects of pre-treatment on the efficacy of the present approach have been evaluated in the pre-clinical setting, using CSC propagation as the measurement. These evaluations considered, in part, the efficacy of simultaneously co-administering three therapeutic agents (e.g., an antibiotic inhibiting the large mitochondrial ribosome, an antibiotic inhibiting the small mitochondrial ribosome, and in this embodiment Vitamin C), through a pre-treatment assay prior to initiating the 3D mammosphere stem cell assay. MCF7 cells were grown as monolayer cultures, and first pre-treated with either Vitamin C alone ("Vit C," 250 µM), or doxycycline and azithromycin ("D+A," 1 µM each), for a period of 7 days. Then, MCF7 cells were harvested with trypsin and re-plated under anchorage-independent growth conditions, in the presence of various combinations of Vitamin C, doxycycline and azithromycin. Table 1 below shows that 7 days of pre-treatment with either Vitamin C alone or the combination of doxycycline and azithromycin (D+A), rendered the subsequent administration of the triple combination significantly less effective. Mechanistically, it appears that the pre-treatments effectively pre-conditioned MCF7 cells to the effects of the triple combination of doxycycline, azithromycin, and Vitamin C. This may be due to MCF7 cells' ability to induce oxidative stress, driving an anti-oxidant response. Given these clinical results, it appears embodiments of the present approach that simultaneously co-administer all three therapeutic agents appear to have the most significant impact on the CSC population, and are preferred. For example, in one embodiment, simultaneously co-administering doxycycline (1 µM), azithromycin (1 µM) and Vitamin C (250 µM), will be more effective than sequentially administering the components. However, some embodiments may call for administering therapeutic agents within a narrow window, such as 1-3 hours, over multiple days (e.g., 3-7 days in some embodiments, 4-14 days in some embodiments). The antibiotics may be administered in oral form (e.g., pill or tablet), while the Vitamin C is administered intravenously in some embodiments. In others, all three therapeutic agents may be administered orally, either as separate pills or tabs, or as a single concoction containing each therapeutic agent.

TABLE 1

Temporal effects of administering components of the present approach.

| Monolayer Treatment (7-days) | Suspension Treatment (5-days) | MFE (% Inhibition ± SD) |
|---|---|---|
| No pre-treatment | D + A + Vit C | 90.71% ± 4.30**** |
| Vit C | Vit C | 49.25% ± 8.00** |
| Vit C | D + A | 37.98% ± 5.68** |
| Vit C | D + A + Vit C | 68.15% ± 7.72*** |
| D + A | D + A | 40.64% ± 5.62** |
| D + A | Vit C | 39.12% ± 4.73** |
| D + A | D + A + Vit C | 64.25% ± 3.95*** |

Components administered include doxycycline (1 µM), azithromycin (1 µM) and Vitamin C (250 µM). Superscript indicates p < 0.01, *indicates p < 0.001, and ****indicates p < 0.0001.

These results demonstrate that the inhibitory effects of doxycycline on CSC population can be potentiated by combination with another FDA-approved antibiotic, namely azithromycin, and a dietary supplement, Vitamin C (a mild pro-oxidant). Accordingly, the present approach provides pharmaceutical compositions having one or more antibiotics inhibiting the large mitochondrial ribosome, one or more antibiotics inhibiting the small mitochondrial ribosome, and one or more pro-oxidants. Embodiments may include, for example, azithromycin, doxycycline, and Vitamin C. Future clinical trials and further evaluation are planned, to generate further data on the embodiment disclosed and suggested herein.

In an example embodiment for anti-aging, treatment according to the present approach was prescribed over a multi-month period. The composition included azithromycin as the first antibiotic inhibiting the large mitochondrial ribosome, doxycycline as the second antibiotic inhibiting the small mitochondrial ribosome, and Vitamin C as a pro-oxidant for inducing mitochondrial oxidative stress. Over a five-week period, azithromycin was administered at 250 mg twice per week, doxycycline was administered at 100 mg twice per day, and Vitamin C was administered at 500 mg once per day. The subject—a 77-year old male—reported increased hair growth, mental awareness and acuity, strength and stamina, and sexual drive, as well as improved vision, hearing, speech, hand-eye coordination and balance, and an overall feeling of well-being and positive energy. After three months of the triple combination treatment, the recipient reported the disappearance of a clinically-palpable prostate nodule following treatment according to the present approach, without any other medications or changes in diet, exercise, and routine.

Some embodiments may take the form of a composition, such as a pharmaceutical composition having a pharmaceutically-effective amount of each therapeutic agent. The composition may be for anti-aging therapy, including one or more of treating senescence, preventing senescence, and/or delaying the onset of senescence. The composition may be for treating cancer through eradicating cancer stem cells, including, e.g., energetic cancer stem cells, circulating tumor cells, and therapy-resistant cancer cells. The composition may be for sensitizing cancer stem cells to radiotherapy, photo therapy, and/or chemotherapy. The composition may be for treating and/or preventing tumor recurrence, metastasis, drug resistance, radiotherapy resistance, and cachexia. Embodiments of the composition may include as active ingredients, a first therapeutic agent that inhibits mitochondrial biogenesis and targets the large mitochondrial ribosome, a second therapeutic agent that inhibits mitochondrial biogenesis and targets the small mitochondrial ribosome, and a third therapeutic agent that induces mitochondrial oxidative stress. For example, in some embodiments, the first therapeutic agent is azithromycin, the second therapeutic agent is doxycycline, and the third therapeutic agent is Vitamin C (or an ascorbic acid derivative). The concentration of at least one of, and in some embodiments both, the first and second therapeutic agents may be sub-antimicrobial. For example, in some embodiments the concentration of both azithromycin and doxycycline is sub-antimicrobial. In some embodiments, the third therapeutic agent is Vitamin C at a concentration sufficient to achieve a peak Vitamin C concentration between 100 $\mu M$ and 250 $\mu M$ in at least one of blood, serum, and plasma. In a demonstrative anti-aging example, azithromycin may be administered at 250 mg once or twice per week, doxycycline may be administered at 100 mg once or twice per day, and Vitamin C may be administered at 500 mg once per day. The dosing may be adjusted for patient body mass and metabolism, and it should be appreciated that commercially-available doses may be used without departing from the present approach.

Under the present approach, one or more antibiotics inhibiting the large mitochondrial ribosome and one or more antibiotics inhibiting the small mitochondrial ribosome, may be used. Antibiotics in the erythromycin (or macrolide) family, including erythromycin, azithromycin, roxithromycin, telithromycin, and clarithromycin, inhibit the large mitochondrial ribosome. Other therapeutic agents that inhibit the large mitochondrial ribosome include other members of the macrolide family, members of the ketolide family, members of the amphenicol family, members of the lincosamide family, members of the pleuromutilin family, as well as derivatives of these compounds. It should be appreciated that a derivative may include one or more mitochondrial-targeting signals, as discussed herein. Antibiotics in the tetracycline family, including tetracycline, doxycycline, tigecycline, eravacycline, and minocycline, inhibit the small mitochondrial ribosome. Other therapeutic agents that inhibit the small mitochondrial ribosome include other members of the tetracycline family, members of the glycylcycline family, members of the fluorocycline family, members of the aminoglycoside family, members of the oxazolidinone family, as well as derivatives of these compounds. It should be appreciated that a derivative may include one or more membrane-targeting signals and/or mitochondrial-targeting signals. Preferred embodiments of the present approach include azithromycin and doxycycline, though it should be appreciated that other antibiotics may be used. Further, one or more of the antibiotics may, in some embodiments, be chemically modified with at least one membrane-targeting signal and/or mitochondria-targeting signal.

As discussed above, embodiments of the present approach may include one or more pro-oxidants. A pro-oxidant is a compound that induces oxidative stress in an organism, through inhibiting antioxidant systems and/or generating reactive oxygen species. Mitochondrial oxidative stress can damage cells, and in CSCs and senescent cells cause a shift towards mitochondrial biogenesis. Some vitamins are pro-oxidant when they operate as a reducing agent. Vitamin C, for example, is a potent antioxidant preventing oxidative damage to lipids and other macromolecules, but behaves as a pro-oxidant in various conditions. For example, Vitamin C at a low concentration (e.g., in a pharmaceutical composition for oral administration), may be administered in an amount or concentration sufficient to achieve peak Vitamin C concentration in at least one of the blood, serum, and plasma, of about 500 $\mu M$ to about 100 $\mu M$, and in some embodiments about 400 $\mu M$ to about 150 $\mu M$; and in some embodiments about 300 $\mu M$ to about 200 $\mu M$, and in some embodiments, about 250 $\mu M$) and in the presence of metal ions, induces mitochondrial oxidative stress. It is understood that the peak Vitamin C concentration in blood/serum/plasma from oral administration is about 250 $\mu M$, whereas the peak concentration may be significantly higher through intravenous administration. Thus, as another example of the present approach, some embodiments in which Vitamin C is administered orally may use sufficient Vitamin C to achieve a Vitamin C concentration in the blood, serum, and/or plasma, of about 100 $\mu M$ to about 250 $\mu M$. In this context, the term "about" should be understood as an approximation of ±10 $\mu M$, but may depend on the accuracy and precision of the method used to measure blood, serum, and/or plasma concentration. Some embodiments may include sufficient Vitamin C to achieve a Vitamin C concentration in the blood, serum, and/or plasma, of 100 $\mu M$ to 250 $\mu M$. It should be appreciated that the suitable dose of Vitamin C may depend on the other components used in the present approach, and therefore the person of ordinary skill may evaluate the appropriate dose for a given embodiment, using methods known in the art. In addition to Vitamin C, a number of ascorbate derivatives may have pro-oxidant behaviors in certain conditions. For example, ascorbate can reduce metal ions and generate free radicals through the fenton reaction. The ascorbate radical is normally very stable, but becomes more reactive especially in the presence of metal ions, including iron (Fe), allowing the ascorbate radical to become a much more powerful pro-oxidant. As mitochondria are particularly rich in iron, they could become a key target of the pro-oxidant effects of Vitamin C. Vitamin C is highly concentrated within mitochondria. For example, when U937 cells (a human leukemia cell line) were incubated for only 15 minutes in media containing 3 $\mu M$ Vitamin C, it was efficiently transported to the mitochondria, reaching a level of 5 mM (representing an approximately 1,700-fold increase relative to the dose). Mitochondrial transport of Vitamin C is accomplished by the sodium-coupled Vitamin C transporter 2 (SCVCT2), also known as SLC23A2, although other novel mitochondrial transporters have been suggested.

Other pro-oxidant therapeutics may be used, in connection with or as an alternative to Vitamin C. As many current chemotherapeutic agents, as well as targeted radiation, all kill cancer cells, via their pro-oxidant actions, then combined inhibition of mitochondrial biogenesis could be used as an add-on to conventional therapy and would be predicted to improve their efficacy. There are other therapeutic agents known to behave as pro-oxidants in cancer cells, generating reactive oxygen species. There are 9 classes of chemotherapeutics that are associated with oxidative stress: anthracyclines, platinum/paladium-complexes, alkylating agents, epipodophyllotoxins, camptothecins, purine/pyrimindine analogs, anti-metabolites, taxanes, and *vinca* alkaloids. For example, anti-cancer therapeutics adriamycin (and other anthracyclines), bleomycin, and cisplatin, have demonstrated specific toxicity towards cancer cells. Thus, in some embodiments an agent is used to induce mitochondrial oxidative stress, in combination with an antibiotic that inhibits the large mitochondrial ribosome and an antibiotic that inhibits the small mitochondrial ribosome. Further investigations are planned to identify additional therapeutic agents having pro-oxidant effects, as well as the timing of administering the alternative agent that induces mitochondrial oxidative stress. However, Vitamin C clearly has fewer side effects and generally has a better safety profile than chemotherapeutic agents. It should be appreciated that pro-oxidant agents may be used without departing from the present approach.

CSCs have a significantly increased mitochondrial mass, which contributes to their ability to undergo anchorage-independent growth. Hence, the use of inhibitors of mitochondrial biogenesis, together with Vitamin C, could ultimately prevent CSC mitochondria from fully recovering from the pro-oxidant effects of Vitamin C, as these target cells would be unable to re-synthesize new mitochondria. Under metabolically restricted conditions, cancer cells would undergo "frustrated" or "incomplete" mitochondrial biogenesis. This assertion is directly supported by the Seahorse flux analysis data shown in FIGS. 11A, 11B, and 12A-12F, revealing i) reduced mitochondrial metabolism, ii) increased compensatory glycolytic function, and iii) severe ATP depletion. Previous studies have shown that Vitamin C alone increases mitochondrial ATP production by up to 1.5-fold, in the rat heart, under conditions of hypoxia. In addition, Vitamin C is a positive regulator of endogenous L-carnitine biosynthesis, an essential micro-nutrient that is required for mitochondrial beta-oxidation. As such, these findings are consistent with the current results showing that Vitamin C alone is indeed sufficient to increase mitochondrial ATP production, by up to 2-fold, in MCF7 cells.

Figure 13:
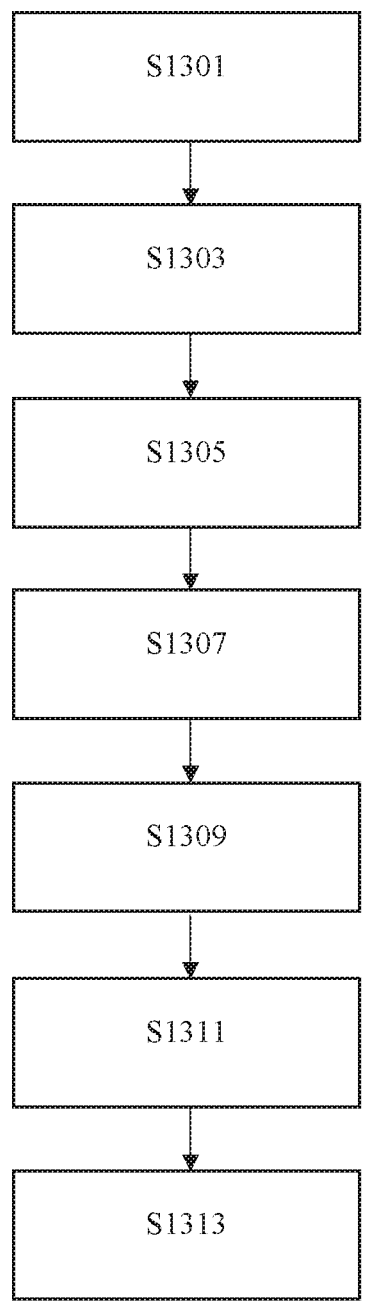
FIG. 13 illustrates a therapeutic mechanism according to an embodiment of the present approach.

FIG. 13 illustrates the therapeutic mechanism according to an embodiment of the present approach. This process may be used for, as examples, eradicating CSCs in a sample or organism, anti-cancer therapy, preventing and/or eliminating recurrence and metastasis, treating senescence, and eradicating senescent cells in a sample or organism. This process may also be used for anti-aging therapy. Under this mechanism, Vitamin C is present under conditions that promote pro-oxidant behavior S1301. The concentration of Vitamin C administered can be considered a relatively low dose. For example, oral Vitamin C sufficient to achieve a blood/plasma/serum level between 100 µM and 250 µM may be appropriate. Mitochondria are rich in iron, and CSCs have a high mitochondria concentration. Due to the high iron content, Vitamin C as a pro-oxidant induces mitochondrial oxidative stress in CSCs or senescent cells 1303, generating reactive ascorbate radicals. In response to the mitochondrial oxidative stress, CSCs and senescent cells shift towards mitochondrial biogenesis 1305. However, the presence of an antibiotic inhibiting the large mitochondrial ribosome and an antibiotic inhibiting the small mitochondrial ribosome 1307, such as azithromycin and doxycycline, prevent CSCs and senescent cells from sufficient mitochondrial biogenesis to recover from the mitochondrial oxidative stress. This results in a mitochondrial catastrophe in CSCs or senescent cells 1309. CSCs and senescent cells then experience ATP depletion 1311, and ultimately die (e.g., through apoptosis) 1313.

The therapeutics in an embodiment of the present approach may be used in the form of usual pharmaceutical compositions which may be prepared using one or more known methods. For example, a pharmaceutical composition may be prepared by using diluents or excipients such as, for example, one or more fillers, bulking agents, binders, wetting agents, disintegrating agents, surface active agents, lubricants, and the like as are known in the art. Various types of administration unit forms can be selected depending on the therapeutic purpose(s). Examples of forms for pharmaceutical compositions include, but are not limited to, tablets, pills, powders, liquids, suspensions, emulsions, granules, capsules, suppositories, injection preparations (solutions and suspensions), topical creams, nano-particles, liposomal formulations, and other forms as may be known in the art. In some embodiments, the therapeutic agents may be encapsulated together. As additional examples, doses in the form of nano-particles or nano-carriers may be used under the present approach, such as liposomes containing fatty acids, cholesterol, phospholipids (e.g., phosphatidly-serine, phosphatidyl-choline), mesoporous silica, and helicene-squalene nano-assemblies. For the purpose of shaping a pharmaceutical composition in the form of tablets, any excipients which are known may be used, for example carriers such as lactose, white sugar, sodium chloride, glucose, urea, starch, calcium carbonate, kaolin, cyclodextrins, crystalline cellulose, silicic acid and the like; binders such as water, ethanol, propanol, simple syrup, glucose solutions, starch solutions, gelatin solutions, carboxymethyl cellulose, shelac, methyl cellulose, potassium phosphate, polyvinylpyrrolidone, etc. Additionally, disintegrating agents such as dried starch, sodium alginate, agar powder, laminalia powder, sodium hydrogen carbonate, calcium carbonate, fatty acid esters of polyoxyethylene sorbitan, sodium laurylsulfate, monoglyceride of stearic acid, starch, lactose, etc., may be used. Disintegration inhibitors such as white sugar, stearin, coconut butter, hydrogenated oils; absorption accelerators such as quaternary ammonium base, sodium laurylsulfate, etc., may be used. Wetting agents such as glycerin, starch, and others known in the art may be used. Adsorbing agents such as, for example, starch, lactose, kaolin, bentonite, colloidal silicic acid, etc., may be used. Lubricants such as purified talc, stearates, boric acid powder, polyethylene glycol, etc., may be used. If tablets are desired, they can be further coated with the usual coating materials to make the tablets as sugar coated tablets, gelatin film coated tablets, tablets coated with enteric coatings, tablets coated with films, double layered tablets, and multi-layered tablets. Pharmaceutical compositions adapted for topical administration may be formulated as ointments, creams, suspensions, lotions, powders, solutions, pastes, gels, foams, sprays, aerosols, or oils. Such pharmaceutical compositions may include conventional additives which include, but are not limited to, preservatives, solvents to assist drug penetration, co-solvents, emollients, propellants, viscosity modifying agents (gelling agents), surfactants, and carriers. It should be appreciated that Vitamin C, or another ascorbate compound, may be administered through a solutions administered directly into the venous circulation via a syringe or intravenous catheter, as is known in the art.

The present approach may be used to treat and/or prevent tumor recurrence, metastasis, drug resistance, cachexia, and/or radiotherapy resistance. Anti-cancer treatments often fail because the tumor recurs or metastasizes, particularly after surgery. Also, drug resistance and radiotherapy resistance are common reasons for cancer treatment failure. It is believed that CSC mitochondrial activity may be, at least in part, responsible for these causes of treatment failure. Embodiments of the present approach may be used in situations where conventional cancer therapies fail, and/or in conjunction with anti-cancer treatments to prevent failure due to tumor recurrence, metastasis, chemotherapy resistance, drug resistance, and/or radiotherapy resistance.

As mentioned, embodiments of the present approach may also be used to prevent, treat, and/or reverse drug resistance in cancer cells. Drug resistance is thought to be based, at least in part, on increased mitochondrial function in cancer cells. In particular, cancer cells demonstrating resistance to endocrine therapies, such as tamoxifen, are expected to have increased mitochondrial function. Embodiments of the present approach inhibit mitochondrial function, and therefore are useful in reducing and, in some cases reversing, drug resistance in cancer cells. Thus, in instances where drug resistance is indicated, embodiments of the present approach may be administered. A pharmaceutical composition as discussed herein may be administered prior to, and/or in conjunction with, and/or following, a conventional chemotherapy treatment. Additionally, mitochondrial function inhibitors that target the mitochondrial ribosome may also target bacteria and pathogenic yeast, target senescent cells (and thus provide anti-aging benefits), function as radiosensitizers and/or photo-sensitizers, sensitize bulk cancer cells and cancer stem cells to chemotherapeutic agents, pharmaceuticals, and/or other natural substances, such as dietary supplements and caloric restriction.

As discussed above, the present approach also has anti-aging efficacy. Regarding anti-aging benefits, senescent cells are toxic to the body's normal healthy eco-system. The present approach may be used as an anti-aging therapeutic and senolytic to selectively kill senescent cells and reduce the population of cells harboring accumulated oxidative damage and/or damaged DNA, while sparing normal tissue cells. Selectively killing senescent cells may: 1) prevent aging-associated inflammation by preventing acquisition of a senescence-associated secretory phenotype (SASP), which turns senescent fibroblasts into pro-inflammatory cells that have the ability to promote tumor progression; 2) facilitate tissue repair and regeneration; and/or 3) increase organismal life-span and health-span. Embodiments may also be used to selectively kill senescent cancer cells that undergo oncogene-induced senescence because of the onset of oncogenic stress.

Reducing cellular accumulated oxidative damage and damaged DNA allows healthy, normal cells to proliferate. As a result, the present approach may be used to improve and/or increase one or more of hair regeneration, hearing, vision, memory, mental acuity, joint mobility, muscle growth, muscular strength, muscular endurance, speed, balance, agility, and sexual performance in mammals. These improvements may be more pronounced in patients exhibiting higher degrees of age-related side-effects, and in older patients. As an example, a 70-year old human may experience greater improvements and increases than a 50-year old human. Viewed from another angle, the present approach has the potential to restore hair growth and natural hair color, restore muscular coordination and gait, restore overall mobility, increase muscle mass, increase grip strength, increase concentration ability and mental clarity, increase learning and memory, and result in an overall feeling of well-being and positive energy in mammals that would otherwise suffer from aging side-effects. This return to vitality occurs, at least in part, from a combination of the selective eradication of senescent cells, CSCs, and cells bearing accumulated oxidative damage and damaged DNA, provided by the present approach. Some embodiments of the present approach have demonstrated a reduction in gray hair, overall frailty, forgetfulness, and general aches and pains, as normal, healthy cells are allowed to proliferate. Additional studies and trials are underway to more thoroughly understand and quantify the benefits of the compositions and methods of the present approach.

Embodiments of the present approach also have implications for improving health-span and life-span. Azithromycin, by itself, is an FDA-approved drug with remarkable senolytic activity that targets and removes senescent fibroblasts, such as myo-fibrobasts. This senolytic activity has considerable efficiency, approaching nearly 97%. The accumulation of pro-inflammatory senescent cells is thought to be the primary cause of many aging-associated diseases, such as heart disease, diabetes, dementia and cancer, for example. Since cancer-associated fibroblasts (CAFs) are senescent myo-fibroblasts, with tumor promoting activity, triple combination embodiments of the present approach with Azithromycin may also effectively target the glycolytic tumor stroma of aggressive and metastatic cancers, especially those bearing the metabolic hallmarks of the "Reverse Warburg Effect." In some embodiments, the composition prevents acquisition of a senescence-associated secretory phenotype. In some embodiments, the composition facilitates tissue repair and regeneration. In some embodiments, the composition increases at least one of organismal life-span and health-span.

Figure 18:
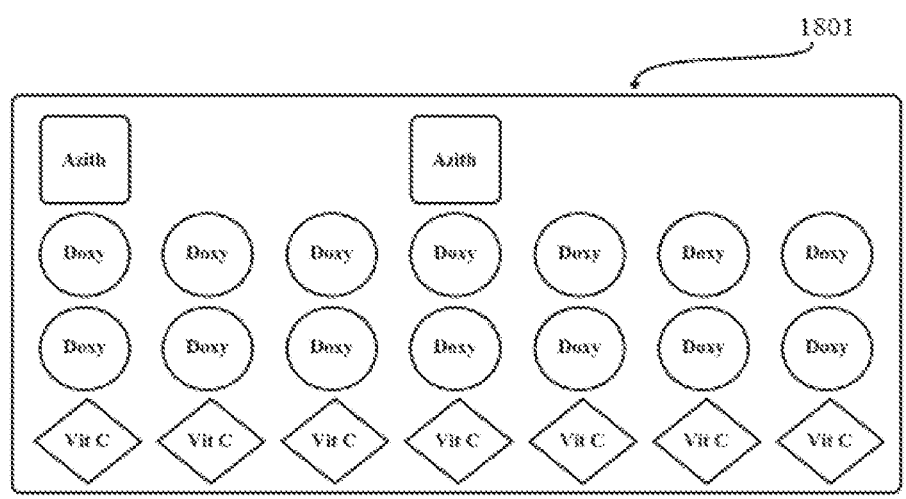
FIG. 18 illustrates an anti-aging kit according to an embodiment of the present approach.

Some embodiments may take the form of an anti-aging kit. The anti-aging kit may contain one or more components according to the present approach. For example, an anti-aging kit may contain a first antibiotic inhibiting the large mitochondrial ribosome, a second antibiotic inhibiting the small mitochondrial ribosome, and a pro-oxidant or an agent inducing mitochondrial oxidative stress. The anti-aging kit may contain enough doses of each component for a specific treatment period or a predetermined time, such as one week or one month. FIG. 18 shows an example anti-aging kit 1401 according to one embodiment. In this embodiment, anti-aging kit 1801 includes one week of doses; 2 azithromycin tablets ("Azith"), 14 doxycycline tablets ("Doxy"), and 7 Vitamin C tablets ("Vit C"). The amount of each component may be as described herein. Anti-aging kit 1401 may include time, date, or day indicators to confirm when each component should be taken, as well as other reminders that may be appropriate. It should be appreciated that an anti-aging kit may include enough doses for shorter or longer periods, such as a two-week treatment or a one-month treatment.

The present approach also advantageously targets CSC and senescent cell phenotypes over normal healthy cells. The target cancer cell may be at least one of a senescent cell, a CSC, an energetic cancer stem cell (e-CSC), a circulating tumor cell (CTC, a seed cell leading to the subsequent growth of additional tumors in distant organs, a mechanism responsible for a large fraction of cancer-related deaths), and a therapy-resistant cancer cell (TRCC, a cell that has developed a resistance to one or more of chemotherapies, radiotherapies, and other common cancer treatments). As described in Applicant's U.S. Provisional Patent Application Nos. 62/686,881, filed Jun. 19, 2018, and 62/731,561, filed Sep. 14, 2018, and incorporated by reference in their entirety, e-CSCs represent a CSC phenotype associated with proliferation. In addition to bulk cancer cells and CSCs, it should be appreciated that the present approach may be used to target a hyper-proliferative cell sub-population that the inventors refer to as e-CSCs, which show progressive increases in sternness markers (ALDH activity and mammosphere-forming activity), highly elevated mitochondrial mass, and increased glycolytic and mitochondrial activity. Compositions having a first antibiotic inhibiting the large mitochondrial ribosome, and a second antibiotic inhibiting the small mitochondrial ribosome, may be administered with a pro-oxidant, to target such cancer cell phenotypes, and beneficially prevent, treat, and/or reduce tumor recurrence, metastasis, drug resistance, radiotherapy resistance, and/or cachexia. Chemically modifying one or more of those therapeutic agents with a membrane-targeting signal and/or a mitochondria-targeting signal enhances the modified therapeutic agent's uptake in mitochondria, and consequently that agent's potency.

Thus, some embodiments of the present approach may include one or more therapeutic agents chemically modified with a membrane-targeting signal and/or a mitochondria-targeting signal. The membrane-targeting signal may be a fatty acid, and in preferred embodiments, one of palmitic acid, stearic acid, myristic acid, and oleic acid. Examples of mitochondria-targeting signals include lipophilic cations, such as TPP and TPP-derivatives. Applicant's co-pending International Patent Application No. PCT/US2018/062174, filed Nov. 21, 2018, is incorporated by reference in its entirety. Tri-phenyl-phosphonium and its derivatives are effective mitochondria-targeting signals for targeting "bulk" cancer cells, cancer stem cells and "normal" senescent cells (fibroblasts), without killing normal healthy cells. Example TPP-derivatives include: (1) 2-butene-1,4-bis-TPP; (2) 2-chlorobenzyl-TPP; (3) 3-methylbenzyl-TPP; (4) 2,4-dichlorobenzyl-TPP; (5) 1-naphthylmethyl-TPP. It should also be noted that TPP-derivatives may also have derivatives. For example, the mitochondria-targeting compound may be a TPP-derivative being at least one of 2-butene-1,4-bis-TPP; 2-chlorobenzyl-TPP; 3-methylbenzyl-TPP; 2,4-dichlorobenzyl-TPP; 1-naphthylmethyl-TPP; p-xylylenebis-TPP; a derivative of 2-butene-1,4-bis-TPP; a derivative of 2-chlorobenzyl-TPP; a derivative of 3-methylbenzyl-TPP; a derivative of 2,4-dichlorobenzyl-TPP; a derivative of 1-naphthylmethyl-TPP; and a derivative of p-xylylenebis-TPP. Lipophilic cation 10-N-nonyl acridine orange may also be used as a mitochondria-targeting signal in some embodiments. It should be appreciated that these targeting signal examples are non-exhaustive.

The following paragraphs relate to therapeutic agents conjugated with a membrane-targeting signal. Examples of membrane-targeting signals include fatty acids such as palmitate, stearate, myristate, and oleate. Short-chain fatty acids, i.e., fatty acids with less than 6 carbon atoms, may also be used as a membrane-targeting signal. Examples of short-chain fatty acids include formic acid, acetic acid, propionic acid, butyric acid, isobutyric acid, valeric acid, and isovaleric acid. The membrane-targeting signal may also be one or more medium-chain fatty acids, having 6-12 carbon atoms. Preferred embodiments of conjugated therapeutic agents have a fatty acid moiety with at least 11 carbons, and up to 21 carbons.

In some embodiments, the fatty acid moiety in a conjugate compound may comprise the general formula

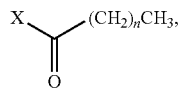

in which X represents the substitution location on a therapeutic agent to which the fatty acid moiety is bound, and 'n' is an integer from 1-20, and preferably from 10-20. As described herein and given this application's use of the term "fatty acid moiety," some embodiments of the present approach may comprise a conjugate compound including a fatty acid moiety having the general formula

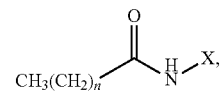

in which X represents the substitution location on a therapeutic agent to which the fatty acid moiety is bound, and 'n' is an integer from 1-20, and preferably from 10-20.

Conjugates having a fatty acid moiety may be synthesized using available techniques in the art. For example, a conjugate of doxycycline and myristic acid may be synthesized through myristoylation. Other techniques for synthesizing conjugates as are known in the art may be used. It should be appreciated that this is not a comprehensive list of membrane-targeting signals, and that an unlisted membrane-targeting signal may be used without departing from the present approach. The fatty acid targeting signal provides an additional benefit with respect to drug delivery. The fatty acid facilitates incorporation of the conjugated compound into lipid-based nanoparticles or a vesicle composed of one or more concentric phospholipid bilayers. For example, U.S. Pat. No. 4,761,288, issued Aug. 2, 1988, describes liposomal drug delivery systems that may be used in some embodiments, and is incorporated by reference in its entirety. These liposome drug delivery embodiments provide more effective drug delivery, as less of the active ingredient is consumed during delivery and initial metabolism.

Figure 14:
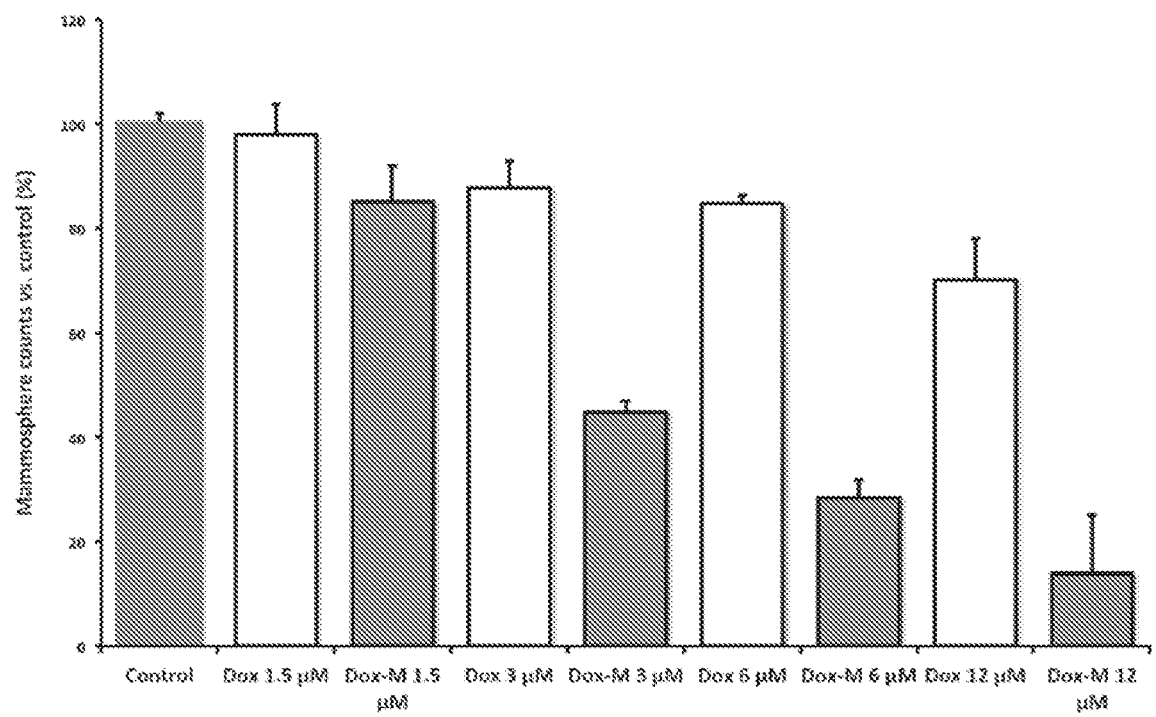
FIG. 14 is a bar graph comparing results from the mammosphere assay on MCF7 cells, for doxycycline and a doxycycline-fatty acid conjugate.

One or more therapeutic agents conjugated with a membrane-targeting signal, such as a fatty acid moiety, may be used in embodiments of the present approach. Although short chain and medium chain fatty acids may be used as targeting signals, fatty acids having at least 11 carbons, and up to 21 carbons, provide the most improvement in the therapeutic agent's CSC inhibition. Conjugates with lauric acid, myristic acid, palmitic acid, and stearic acid, show significant improvement of the therapeutic agent's inhibition and preferential retention properties. As a demonstrative example, embodiments of doxycycline-myristate conjugates have shown more potency than doxycycline alone. FIG. 14 compares results from the mammosphere assay on MCF7 cells, for doxycycline ("Dox") and the doxycycline-myristate conjugate ("Dox-M") shown as compound [1] (note that this disclosure also references compound [1] as a conjugate of doxycycline and myristic acid), below. The data represents mammosphere counts after exposure to a compound, as a percentage of a control. The compounds were tested at concentrations of 1.5 µM, 3 µM, 6 µM, and 12 µM. It can be seen that at each concentration, the doxycycline-myristate conjugate was more potent than unconjugated doxycycline. The potency was significantly more pronounced at concentrations above 3 µM. Similar behavior is seen with other tetracycline family members, and erythromycin family members, conjugated with fatty acids, particularly fatty acid moieties having 11-21 total carbons.

Figure 15:
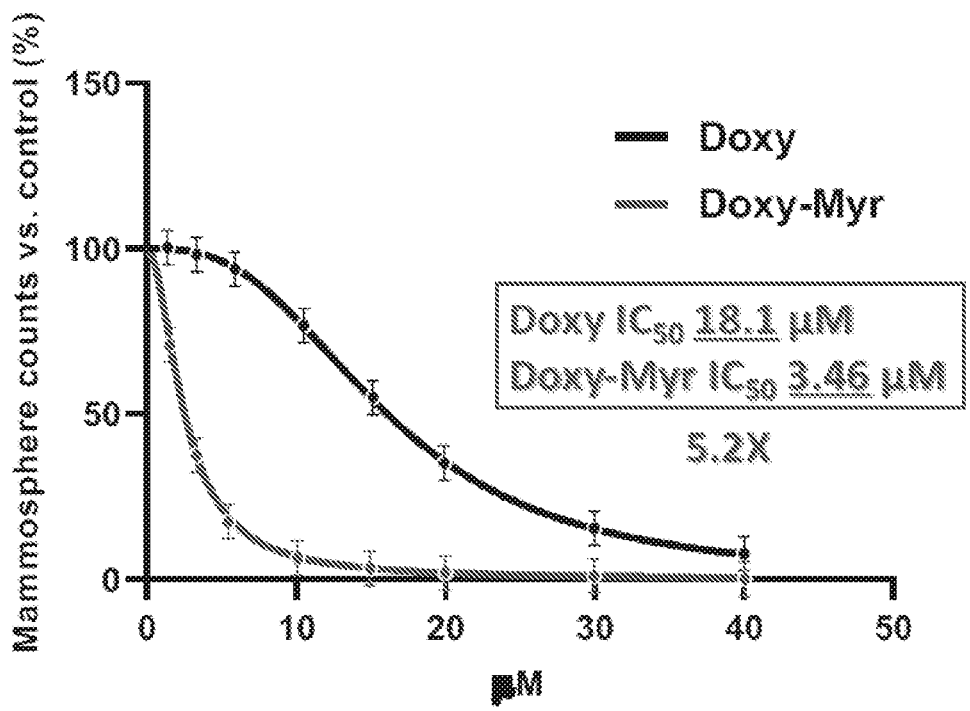
FIG. 15 is a line graph showing mammosphere assay results over a range of concentrations for doxycycline and a doxycycline-fatty acid conjugate.

FIG. 15 is a line graph showing mammosphere assay results over a wider range of compound concentrations for doxycycline and the doxycycline-myristate conjugate shown as compound [1]. The top curve represents mammosphere count (as a percentage compared to a control) for MCF7 cells exposed to doxycycline. The bottom curve represents mammosphere count for MCF7 cells exposed to the doxycycline-myristate conjugate. At 2.5 µM, doxycycline alone had little or no effect in the mammosphere assay on MCF7 cells. In contrast, the doxycycline-myristate conjugate at 2.5 μM inhibited MCF7 mammosphere formation by 40-60% relative to the control. Based on these data, the half maximal inhibitory concentration (IC$_{50}$) for doxycycline is 18.1 μM, and the IC$_{50}$ for the doxycycline-myristate conjugate is 3.46 μM. This demonstrates that the doxycycline-myristate conjugate is over 5 times more potent than doxycycline for inhibiting CSC propagation.

therapeutic agent according to the present approach, and numerous other conjugated therapeutic agents are contemplated. Compound [2], shown below, represents a generic structure of doxycycline conjugated with a fatty acid moiety. The 'n' is an integer from 1-20, and preferably is 10-20. For example, 'n' being 12 results in a conjugate having a myristic acid moiety. Although doxycycline is used in this example, it should be appreciated that other members of the

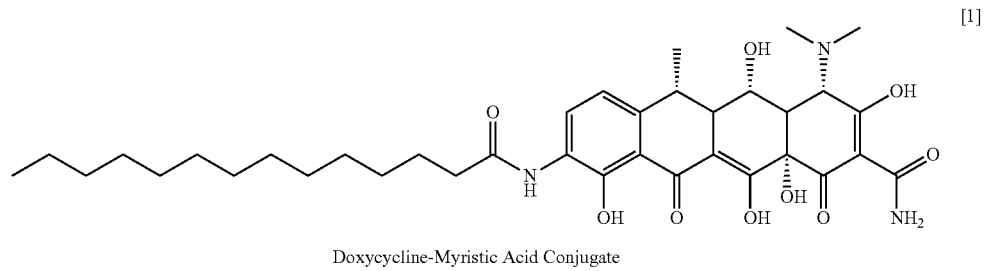 [SMILES: CCCCCCCCCCCCCC(=O)Nc1ccc2c(c1O)C(=O)C1=C(O)[C@]3(O)C(=O)C(C(N)=O)=C(O)[C@@H](N(C)C)C3[C@@H](O)C1[C@H]2C]

Doxycycline-Myristic Acid Conjugate

Figure 16A:
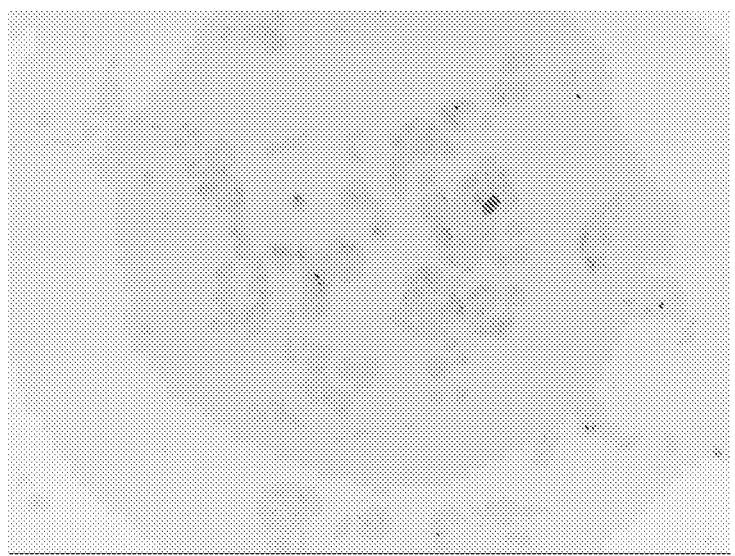
FIGS. 16A-16C are images comparing the cellular retention of a therapeutic agent and targeting signal conjugate, to an unconjugated therapeutic agent.
Figure 16B:
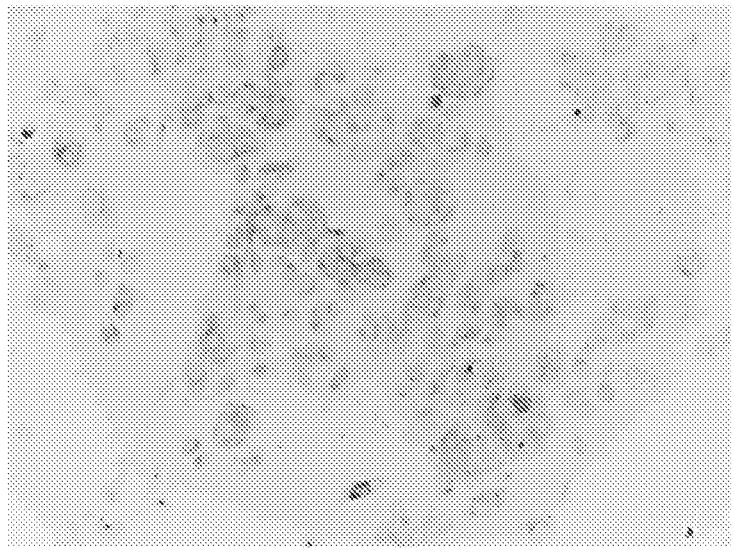
Figure 16C:
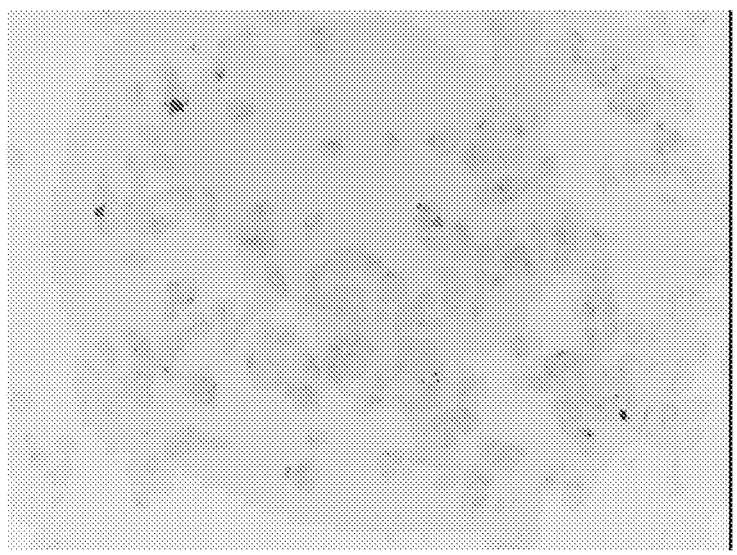

FIGS. 16A-16C are images comparing the cellular retention of the doxycycline-myristate conjugate, to unconjugated doxycycline. MCF7 cells were cultured in tissue culture media in the presence of either therapeutic agent (i.e., the doxycycline-myristate conjugate or unconjugated doxycycline), at a concentration of 10 μM, for 72 hours. Then, the cells were washed with PBS and any therapeutic agent retained within the cells was visualized by green auto-fluorescence, from the excitation of the tetracycline ring structure. Control cells were incubated with vehicle-alone. FIG. 16A is the untreated control, FIG. 16B shows retention of the doxycycline-myristate conjugate compound [1], and FIG. 16C shows retention of doxycycline. The original color in the images has been inverted, to improve reproducibility, and the darker regions of FIG. 16B indicate increased cellular retention of the conjugated therapeutic agent. As can be seen through comparing FIGS. 16A-16C, the darkness and intensity of FIG. 16B indicates that the doxycycline-myristate conjugate has significantly improved cellular retention as compared to doxycycline alone. Comparable results with other therapeutic agents conjugated with other targeting signals should be expected.

Figure 17A:
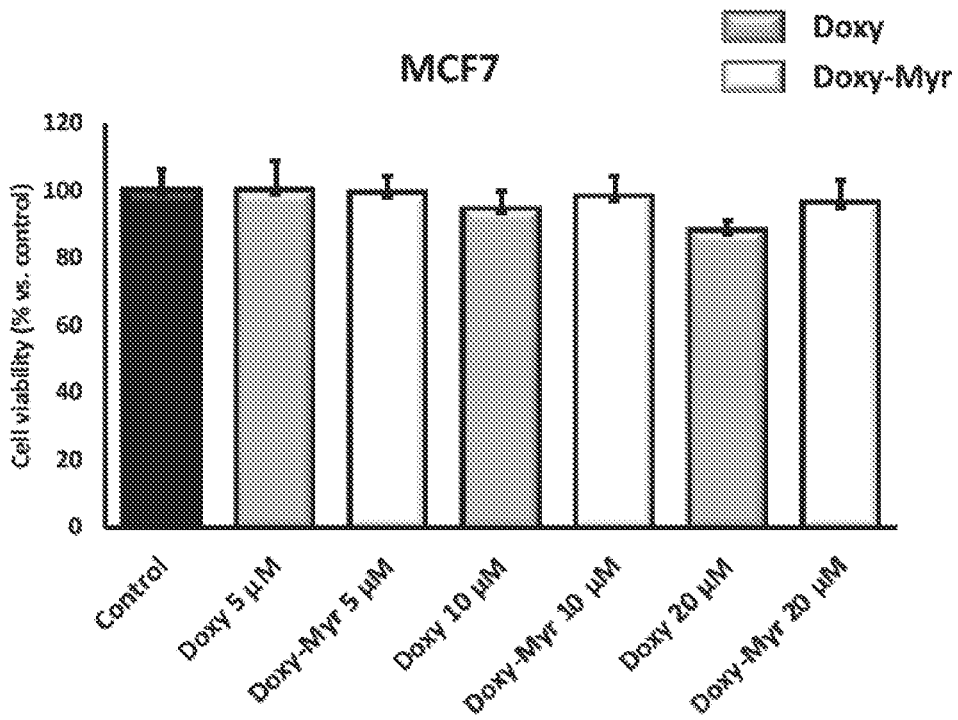
FIGS. 17A and 17B compare cell viability data for a therapeutic agent and targeting signal conjugate, to an unconjugated therapeutic agent, in MCF7 and BJ cells, respectively.
Figure 17B:
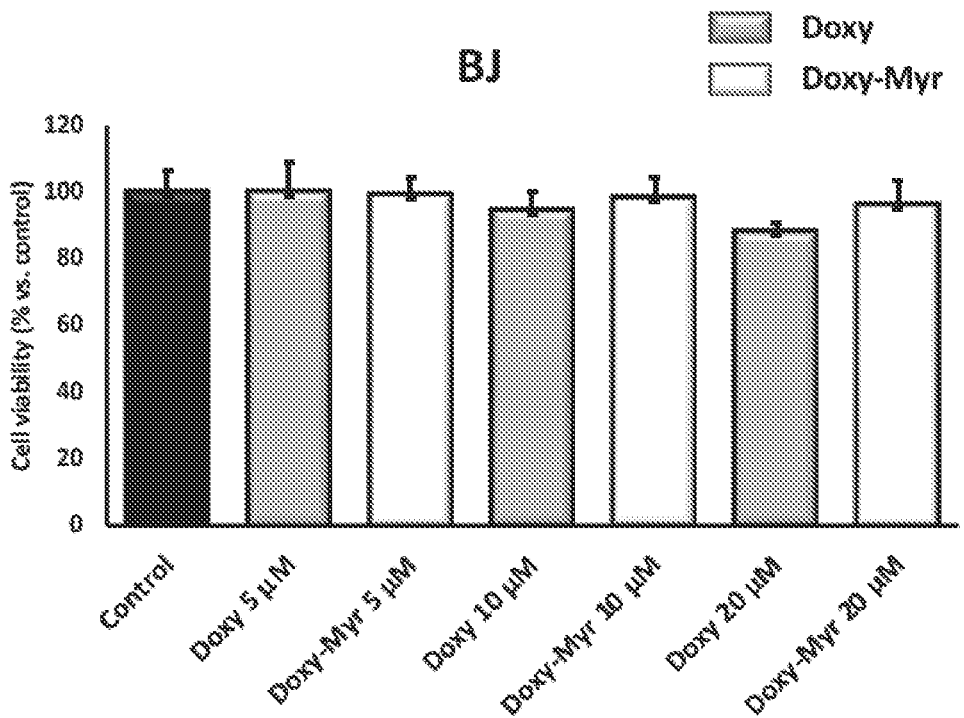

Embodiments of therapeutic agents conjugated with targeting signals have shown less toxicity in bulk cancer cells and normal fibroblasts compared to unconjugated therapeutic agents. For example, FIGS. 17A and 17B show cell viability data for doxycycline and the doxycycline-myristate conjugate shown as compound [1], for bulk MCF7 cells and bulk BJ cells, respectively. The data represents cell viability expressed as a percentage of a control. As can be seen in both FIGS. 17A and 17B, the doxycycline-myristate conjugate is less toxic than doxycycline across the range of concentrations tested, even at concentrations of 20 μM. Similar behavior has been seen in other therapeutic agents conjugated with targeting signals.

It should be appreciated that the doxycycline-myristate conjugate of compound [1] is one example of a conjugated tetracycline family (i.e., antibiotics having a naphthacene core that target the small mitochondrial ribosome) may be used as the therapeutic agent, including, for example and without limitation, tigecycline, minocycline. Compound [3] is a generic chemical structure for tetracycline derivatives, with labels on the naphthacene core rings for use in the current description. It should be understood that tetracycline derivatives have differing functional groups attached to the naphthacene core, and that compound [3] is used primarily to illustrate substitution locations and provide a labelling system. Using the labels shown in compound [3], the fatty acid moiety shown in compound [2] is substituted at what is referred to as the $R_9$ position on the D-ring of the naphthacene core. It should be appreciated that other substitution locations may be used, as well. As shown in the generic structure of compound [3], for example, the $R_7$ and $R_8$ positions of the D-ring are additional options for substitution, for instance. Generally, however, the dimethylamino and amid groups on the A-ring are important for antibiotic activity, which can also depend on stereochemical configuration along the B-ring and C-ring.

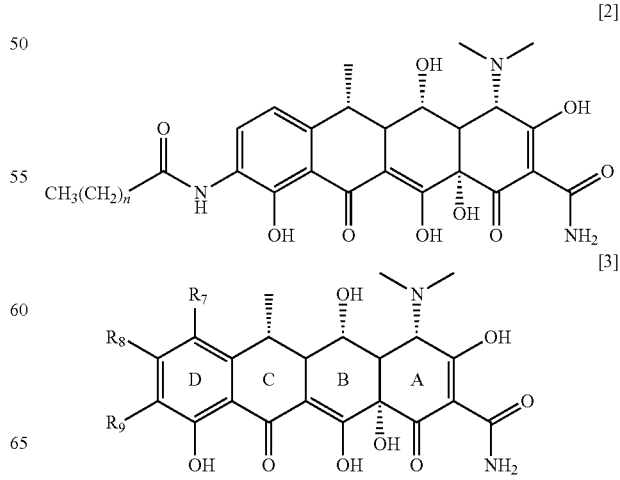

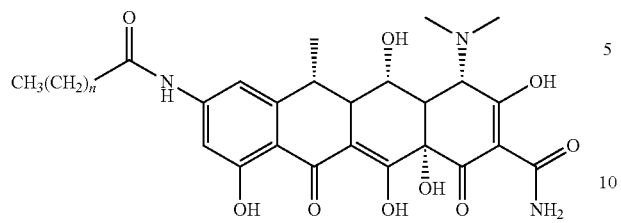

[4]

Compound [4], shown above, is another example of a conjugated therapeutic agent having doxycycline and a fatty acid moiety, according to the present approach. In this embodiment, the fatty acid moiety is substituted at the $R_8$ position of the D-ring. The 'n' is an integer from 1-20, and preferably is 10-20. Compound [5A], shown below, illustrates an example of a tetracycline-fatty acid conjugate according to another embodiment of the present approach. In this example, the fatty acid moiety is substituted at the $R_9$ position of the D-ring, but it should be understood that the fatty acid moiety may be substituted at other locations, as already described. Compound [5B], below, demonstrates another embodiment of a tetracycline family member conjugated with a membrane-targeting signal. In compound [5B], the minocycline structure has a fatty acid moiety substituted at the $R_9$ position of the D-ring. Of course, the fatty acid moiety may be substituted elsewhere, as discussed above. For both compounds [5A] and [5B], the 'n' is an integer from 1-20, and preferably is 10-20.

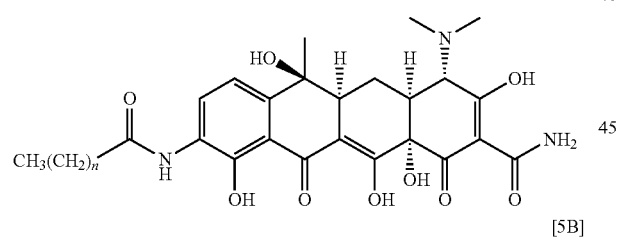

[5A]

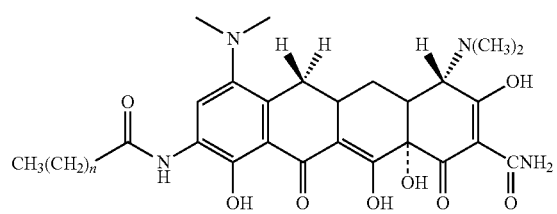

[5B]

The previous examples of therapeutic agent conjugates have involved tetracycline family members. It should be appreciated that conjugates of erythromycin family members with a membrane-targeting signal are also contemplated by the present approach. Compounds [6], [7], and [8] below show the structures for azithromycin, roxithromycin, and telithromycin, examples of FDA-approved antibiotics in the erythromycin family known in the art.

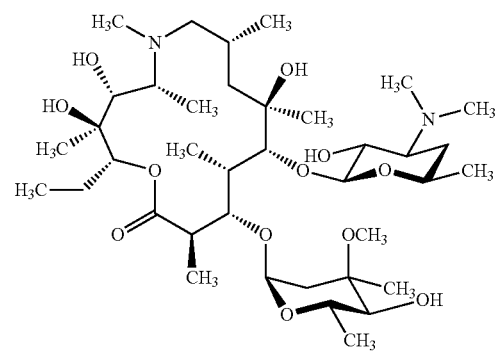

Azithromycin [6]

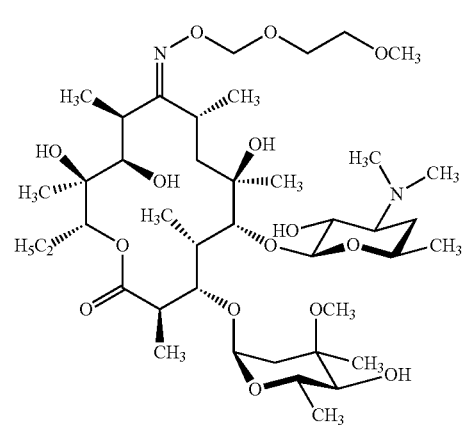

Roxithromycin [7]

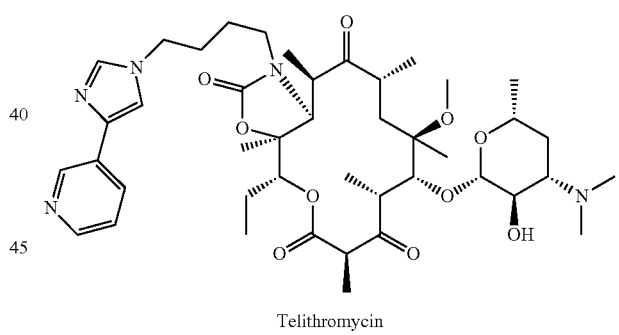

Telithromycin [8]

The macrolide structure provides several potential substitution locations. This description addresses two series of formula for erythromycin family conjugates. Compounds [9A], [9B], [10A], [10B], [11A] and [11B], below, show general structures for azithromycin conjugates, roxithromycin conjugates, and telithromycin conjugates, respectively. Each general structure is shown with multiple R-groups, denoting a potential substitution location. In some embodiments of the present approach, one R-group may be a targeting signal, such as a membrane-targeting signal or a mitochondria-targeting signal, and the remaining R-groups would then be the moiety normally present in the structure (e.g., as shown in compounds [6]-[8]). In some instances, the NH—R group may be $N(CH_3)_2$, as discussed below.

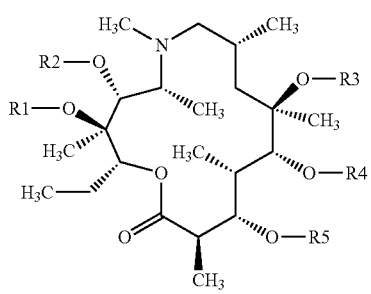

Azithromycin Conjugates I

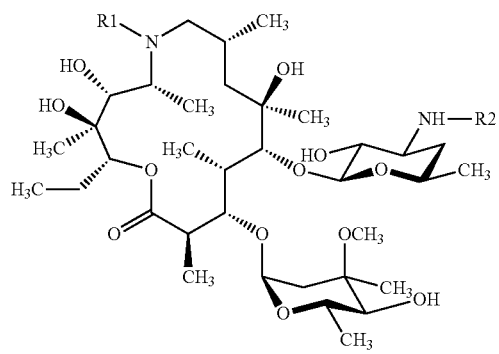

Azithromycin Conjugates II

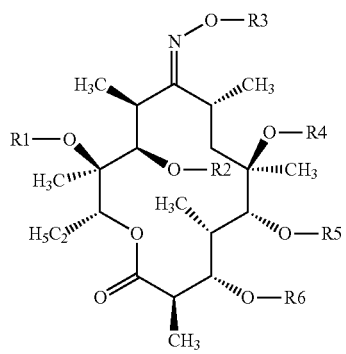

Roxithromycin Conjugates I

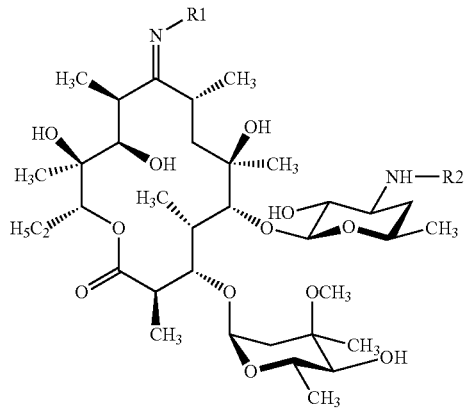

Roxithromycin Conjugates II

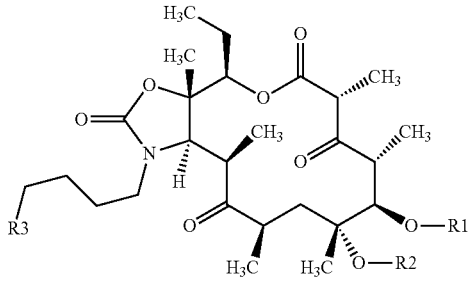

Telithromycin Conjugates I

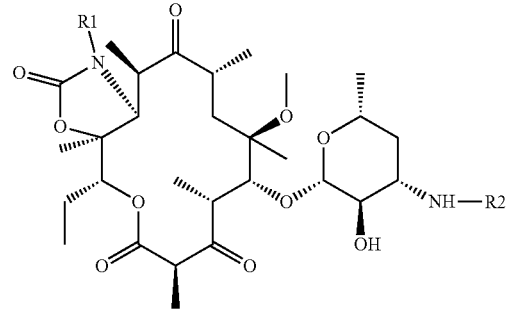

Telithromycin Conjugates II

The first series of general formula for erythromycin family conjugates are represented by compounds [9A], [10A], and [11A]. Starting with compound [9A], $R_2$ in compound [9A], an azithromycin conjugate, may be a fatty acid moiety, and each of $R_1$, $R_3$, $R_4$, and $R_5$ may then be the moiety normally present for azithromycin, as shown in compound [6], namely, H, H, deoxy sugar (desosamine), and a deoxy sugar (cladinose), respectively. It should be appreciated that the targeting signal moiety may instead be substituted at another location instead of $R_2$ as used in this example. Compound [10A] shows a first general formula for roxithromycin conjugates. $R_1$ in compound [10A] may be a fatty acid moiety, and each of $R_2$-$R_6$ may then be the moiety normally present for roxithromycin, as shown in compound [7]. As another example, the telithromycin conjugate of compound [11A], $R_3$ may comprise a targeting signal, and $R_1$ and $R_2$ may then be the moiety normally present for roxithromycin, as shown in compound [8] (e.g., $R_1$ is the aryl-alkyl moiety on the carbamate ring, and —NHR$_2$ becomes —N(CH$_3$)$_2$, i.e., the desosamine sugar ring).

The second series of general formulas shown above demonstrate conjugates according to additional embodiments of the present approach. Compound [9B] shows a second general formula for azithromycin conjugates according to some embodiments, in which functional groups $R_1$ and $R_2$ may be the same or may be different, and one or both is a targeting signal. For example, $R_1$ and/or $R_2$ may be a targeting signal, and if not the same, then the other R remains the same as shown in compound [6]. For instance, $R_1$ may be methyl and $R_2$ may be a targeting signal, such as a fatty acid moiety. As another example, $R_1$ may be a targeting signal and NH—$R_2$ may be —N(CH$_3$)$_2$.

Compound [10B] shows a second general formula for roxithromycin conjugates according to some embodiments, in which functional groups $R_1$ and $R_2$ may be the same or may be different, and one or both may be a targeting signal. For example, $R_1$ and/or $R_2$ may be a fatty acid moiety, as discussed above, and the other may be the same as shown in compound [7]. As another example using compound [10B], $R_1$ may be a methoxy, such as O—CH$_2$—O—(CH$_2$)$_2$—OCH$_3$ present in roxithromycin, and $R_2$ may be a targeting signal, such as a fatty acid moiety. As another example, $R_1$ may be a targeting signal and NH—$R_2$ may be N(CH$_3$)$_2$.

Compound [11B] shows a second general formula for telithromycin conjugates, in which functional groups $R_1$ and $R_2$ may be the same or may be different, and one or both may be a targeting signal. For example, $R_1$ and/or $R_2$ may be a membrane-targeting signal or a mitochondria-targeting signal, as discussed above. For example, $R_1$ may be an alkyl-aryl group, such as

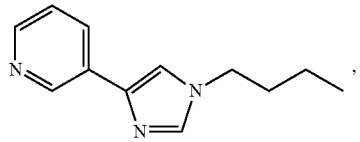

which is present on the telithromycin carbamate ring, and $R_2$ may be a targeting signal. As another example, $R_1$ may be a targeting signal and —NH—$R_2$ may be —N(CH$_3$)$_2$.

Compounds [12A], [13A], and [14A], below, demonstrate specific examples of erythromycin family member conjugates according to the approach, using the first series of general structures for conjugates described above. In compound [12], $R_5$ has been substituted with the general structure for a fatty acid moiety, and the other substitution locations have the normal constituents found on the azithromycin structure. In compound [13], $R_5$ has been substituted with the general structure for a fatty acid moiety, and the other substitution locations have the normal constituents found on the roxithromycin structure. In compound [14], $R_3$ has been substituted with the general structure for a fatty acid moiety, and the other substitution locations have the normal constituents found on the telithromycin structure. In these examples, the 'n' is an integer from 1-20, and preferably is 10-20. Embodiments of compounds [12A], [13A], and [14A], in which the fatty acid moiety is myristate, for instance, have demonstrated improvements in CSC inhibition activity and cellular retention over the unconjugated antibiotics. It should be appreciated that this approach may be used to form numerous conjugates of erythromycin family members and targeting signal moieties.

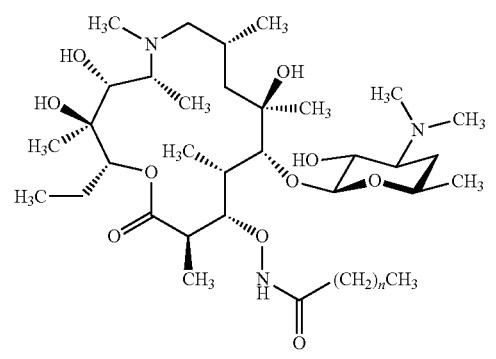

Azithromycin-Fatty Acid Conjugate

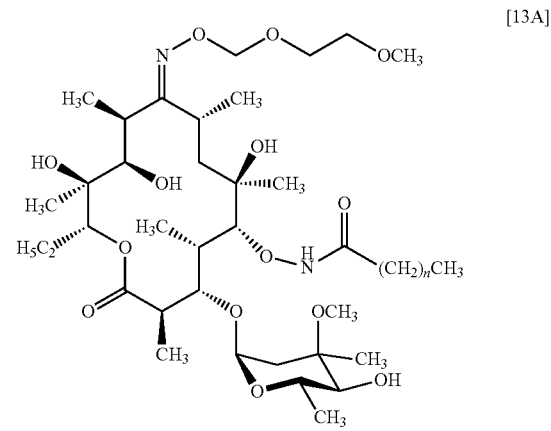

Roxithromycin-Fatty Acid Conjugate

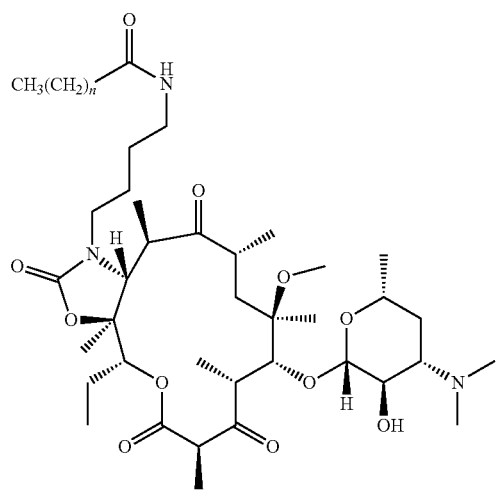

Telithromycin-Fatty Acid Conjugate

Compounds [12B], [13B], and [14B], below, demonstrate specific examples of erythromycin family member conjugates according to the approach, and using the second series of general structures shown above. In compound [12B], $R_1$ has been substituted with the general structure for a fatty acid moiety

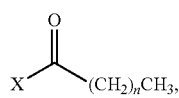

in which 'n' is an integer between 1 and 20, preferably 10 to 20, and the other substitution location has the normal constituent found on the azithromycin structure. In compound [13B], $R_2$ has been substituted with the same fatty acid moiety general structure as in compound [12B], and the other substitution location $R_1$ has the normal constituent found on the roxithromycin structure. As an example based on the second telithromycin conjugate general formula, compound [14B] has the same fatty acid general structure at $R_1$, and NH—$R_2$ is instead $N(CH_3)_2$ as found on the telithromycin structure. In these examples, the 'n' is an integer from 1-20, and preferably is 10 to 20. Embodiments of erythromycin and fatty acid conjugates, such as shown in compounds [12A], [12B], [13A], [13B], [14A], and [14B], in which the fatty acid moiety is myristate, for instance, have demonstrated improvements in CSC inhibition activity and cellular retention over the unconjugated antibiotics. It should be appreciated that this approach may be used to form numerous conjugates of erythromycin family members and targeting signal moieties.

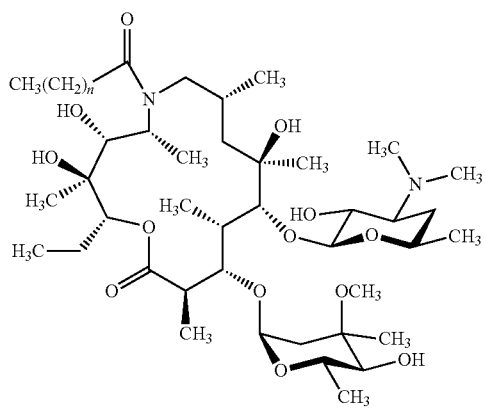

[12B]

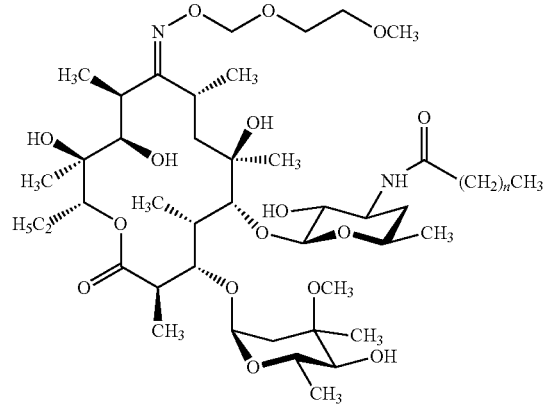

[13B]

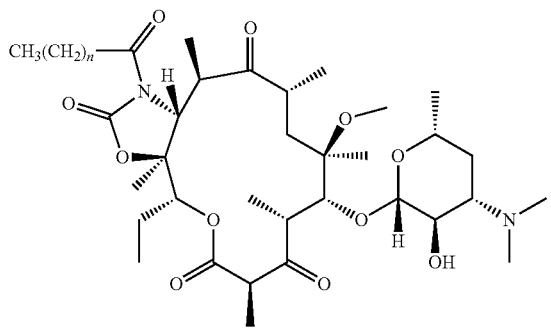

[14B]

Below is an embodiment of a specific example of a conjugate of telithromycin and a fatty acid moiety, using the general structure shown as formula [11B] above. In this example, shown as formula [14C], $R_1$ remains the same as in unconjugated telithromycin, and the fatty acid moiety is at $R_2$, in which n is an integer from 1-20, and preferably is 10 to 20. In a preferred embodiment of formula [14C], n is 12, and the resulting conjugate have demonstrated significant improvements in CSC inhibition activity and cellular retention over the unconjugated antibiotics.

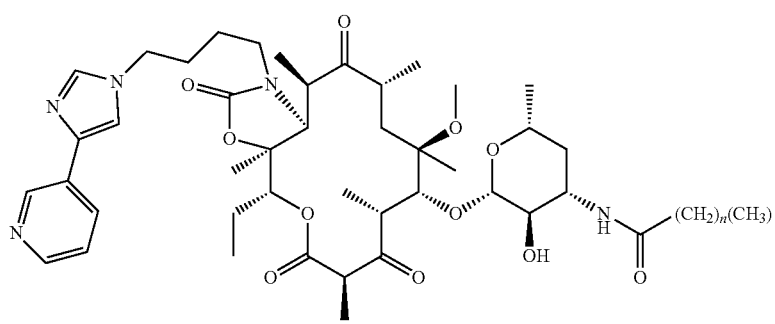

[14C]

Compound [15], shown below, illustrates one embodiment of an erythromycin family member, azithromycin, conjugated with myristate. The fatty acid moiety is substituted at the $R_2$ location in compound [9B], and $R_1$ remains a methyl group. The conjugate shown as compound [15] has demonstrated improved potency and selectivity for CSCs, compared to azithromycin alone, and may be used as a therapeutic agent in embodiments of the present approach.

jugated with a mitochondria-targeting signal, often through the use of a spacer arm and/or a linking group. Examples of mitochondria-targeting signals include lipophilic cations, such as TPP, TPP-derivatives, guanidinium-based moieties, quinolinium-based moieties, and 10-N-nonyl acridine orange. Choline esters, rhodamine derivatives, pyridinium, (E)-4-(1H-Indol-3-ylvinyl)-N-methylpyridinium iodide (F16), and sulfonyl-urea derivatives such as diazoxide, may

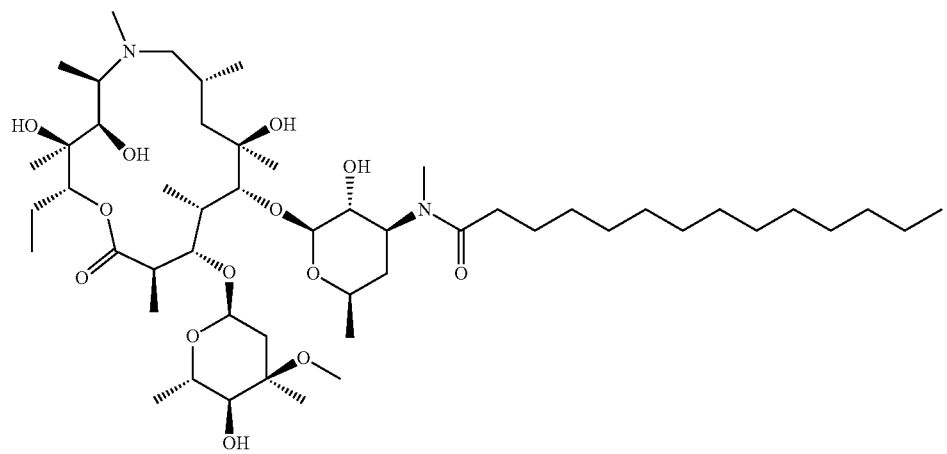

[15]

Before turning to conjugates with lipophilic cations, a brief discussion of ascorbic acid (Vitamin C) conjugates with fatty acids follows. Some embodiments may use a pro-oxidant therapeutic agent conjugated with a membrane-targeting signal. Other therapeutic agents may be conjugated with a membrane-targeting signal as well. In particular, derivatives of Vitamin C (e.g., ascorbates) may be conjugated with a fatty acid moiety. For example, ascorbyl palmitate is an ester of ascorbic acid and palmitic acid commonly used in large doses as a fat-soluble Vitamin C source and an antioxidant food additive. Embodiments of the present approach may use ascorbyl palmitate as a pro oxidant. Some embodiments of the present approach may use a derivative of Vitamin C conjugated with a targeting signal, with or without therapeutic agents also having a targeting signal moiety. Embodiments in which therapeutic compounds are conjugated with fatty acids for liposomal drug delivery may include ascorbyl palmitate, or other conjugates with a fatty acid, for collective improvement in the packaging and delivery of each therapeutic agent in the embodiment. Compound [5], below, is a generic structure for a Vitamin C derivative conjugated with a fatty acid, in which n is an integer from 1-20, and preferably is 10-20.

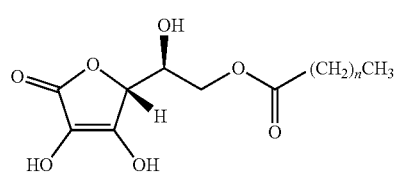

[S]

As discussed above, one or more therapeutic compounds may take the form of an antibiotic conjugated with a mitochondria-targeting signal. The following paragraphs describe embodiments in which a therapeutic agent is conalso be used as a mitochondria-targeting signal in some embodiments. Examples of TPP-derivatives include, for example, 2-butene-1,4-bis-TPP; 2-chlorobenzyl-TPP; 3-methylbenzyl-TPP; 2,4-dichlorobenzyl-TPP; 1-naphthyl-methyl-TPP; or p-xylylenebis-TPP. The TPP-derivative compound 2-butene-1,4-bis-TPP may be used in some preferential embodiments. It should be appreciated that this is not a comprehensive list of mitochondria-targeting signals, and that an unlisted mitochondria-targeting signal may be used without departing from the present approach.

The following examples are used to demonstrate conjugates of tetracycline compounds with a mitochondria-targeting signal. The previous description of potential substitution locations (e.g., with respect to compounds [3] and [9A]-[11B]), is applicable to conjugates with mitochondria-targeting signals. In some embodiments, the therapeutic agent may be conjugated with TPP using a linking group and/or a chemical spacer arm, as described above. Additionally, it should be appreciated that numerous linking groups are known in the art, and may be used to form conjugates with mitochondria-targeting signals as described herein. For example, International Patent Application Publication WO 99/26582, corresponding to International Patent Application PCT/NV98/00172, filed Nov. 25, 1998, hereby incorporated by reference in its entirety, describes the use of the formula TPP—X—R Z⁻, in which Z is an anion, X is a linking group, and R is the therapeutic agent. In some embodiments, X may be a $C_{1-6}$ alkyl. As another example, International Patent Application Publication WO 2010/141177, corresponding to International Patent Application PCT/US2010/031455, filed Apr. 16, 2010, and incorporated by reference in its entirety, describes a variety of "linking moiety" examples that may be used in the present approach.

Compound [16A] illustrates a general formula for a tetracycline derivative (in this case, tetracycline) conjugated with a mitochondria-targeting signal (in this case, TPP), through a linking group —NHC(O)— at what is referred to as the $R_9$ position on the D-ring, and a spacer arm $(CH_2)_n$, where 'n' is an integer from 1-20. Compound [16A] below illustrates an example of doxycycline conjugated with the TPP cation, tethered via a demonstrative 5-carbon spacer arm and an amide linking group at the $R_9$ position.

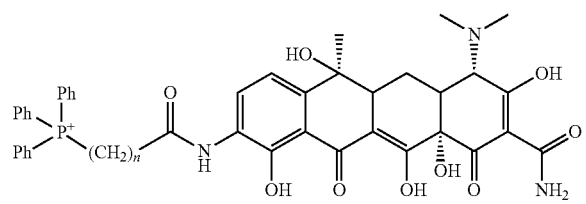

[16A]

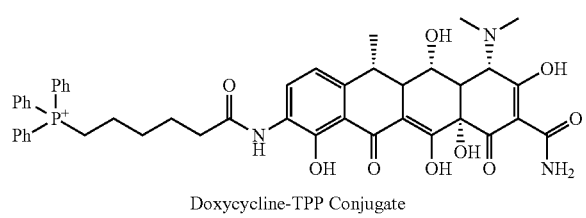

[16B]

Doxycycline-TPP Conjugate

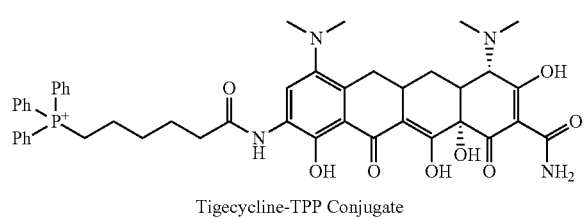

[16C]

Tigecycline-TPP Conjugate

Conjugates of erythromycin family members and mitochondria-targeting signals may be formed as well, using substitution locations shown in compounds [9A]-[11B]. For brevity, those structures will not be repeated, and only one demonstrative embodiment will be provided. Compound [17], shown below, illustrates an erythromycin family member, azithromycin, conjugated with TPP, through a demonstrative 4-carbon spacer arm and an amide linking group. It should be appreciated that numerous other conjugates of erythromycin family members and mitochondria-targeting signals may be formed, as described above.

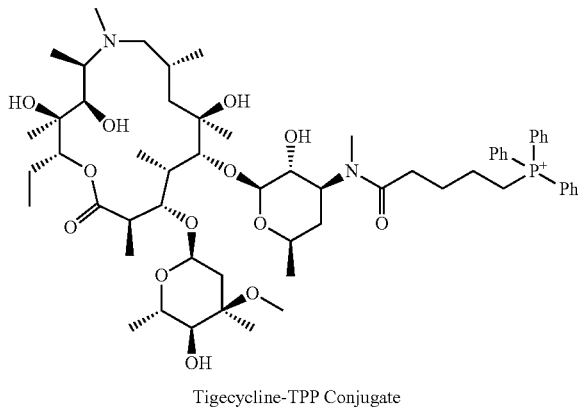

[17]

Tigecycline-TPP Conjugate

The following paragraphs describe examples of methods for synthesizing conjugates according to the present approach. First, two methods were available for preparative HPLC (high performance liquid chromatography). Method A involved an LC column from Phenomenex Kinetex 5 μm EVO C18 100 250×21.2 mm. Gradient eluent: 20-80% acetonitrile/water containing 0.1% formic acid. Time: 0-25 min. Wavelength: 246 nm. Method B also involved an LC column from Phenomenex Kinetex 5 μm EVO C18 100 250×21.2 mm. Gradient eluent: 20-80% acetonitrile/water containing 0.015M $NaH_2PO_4$ and 0.015M oxalic acid (pH7). Time: 0-25 min. Wavelength: 254 nm. Analytical liquid chromatography was performed via LC column. Waters Sunfire C18 30×4.6 mm. Gradient eluent: 3-97% acetonitrile/water containing 0.05% formic acid. Time: 0-6 min.

The following abbreviation are used in the Examples; N,N,N',N'-Tetramethyl-O-(1H-benzotriazol-1-yl)uronium hexafluorophosphate (HBTU), N-methylmorpholine (NMM), dichloromethane (DCM), dimethylformamide (DMF), dimethylsulfoxide (DMSO), O-(6-Chlorobenzotriazol-1-yl)-N,N,N',N'-tetramethyluronium hexafluorophosphate (HCTU), methanol (MeOH), ammonia ($NH_3$).

Example 1—A conjugate of doxycycline and a fatty acid. (4S,5S,6R,12aS)-4-(dimethylamino)-3,5,10,12,12a-pentahydroxy-6-methyl-1,11-dioxo-9-(tetradecanoylamino)-4a,5,5a,6-tetrahydro-4H-tetracene-2-carboxamide (i.e., doxycycline conjugated with myristic acid at $R_9$, as described above and shown below compound [18]). A solution of 9-aminodoxycycline (prepared as described in Barden, Timothy C. et al. "Glycylcyclines". 3. 9-Aminodoxycyclinecarboxamides. J. Med. Chem. 1994, 37, 3205-3211) (0.70 g, 1.5 mmol), tetradecanoic acid (0.36 g, 1.5 mmol), HBTU (0.85 g, 2.25 mmol) and NMM (0.33 ml, 3.0 mmol) in a mixture of DCM (12 ml) and DMF (4 ml) was stirred under nitrogen atmosphere at room temperature for 72 hours. The solvents were evaporated under reduced pressure. The resulting residue was triturated with acetonitrile (40 ml, the precipitation was collected by filtration, was washed with acetonitrile (10 ml), diethyl ether (20 ml) and dried under vacuum. The crude product was dissolved in DMSO and purified by preparative HPLC (Method A) to yield (4S,5S,6R,12aS)-4-(dimethylamino)-3,5,10,12,12a-pentahydroxy-6-methyl-1,11-dioxo-9-(tetradecanoylamino)-4a,5,5a,6-tetrahydro-4H-tetracene-2-carboxamide (0.086 g). LC-MS 670.2 [M+H]⁺, RT 2.78 min.

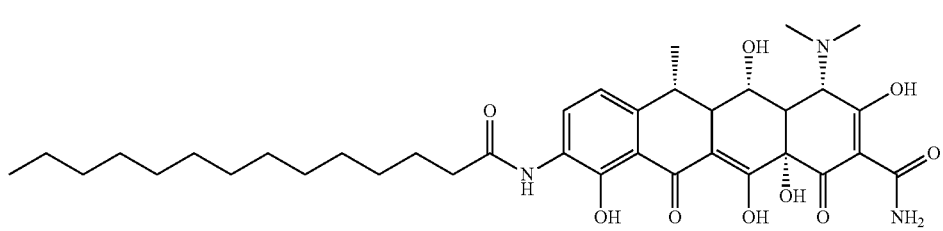

[18]

Example 2—A conjugate of doxycycline and a fatty acid. (4S,5S,6R,12aS)-4-(dimethylamino)-9-(hexadecanoylamino)-3,5,10,12,12a-pentahydroxy-6-methyl-1,11-dioxo-4a,5,5a,6-tetrahydro-4H-tetracene-2-carboxamide. Compound [19], shown below, was prepared following the method in Example 1. LC-MS 698.2 [M+H]+, RT 3.02 min.

Example 5—A precursor for azithromycin conjugates. 2R,3S,4R,5R,8R,10R,11R,12S,13S,14R)-2-ethyl-3,4,10-trihydroxy-13-[(2S,4R,5S,6S)-5-hydroxy-4-methoxy-4,6-dimethyl-tetrahydropyran-2-yl]oxy-11-[(2S,3R,4S,6R)-3-hydroxy-6-methyl-4-(methylamino)tetrahydropyran-2-yl]oxy-3,5,6,8,10,12,14-heptamethyl-1-oxa-6-azacyclopenta-

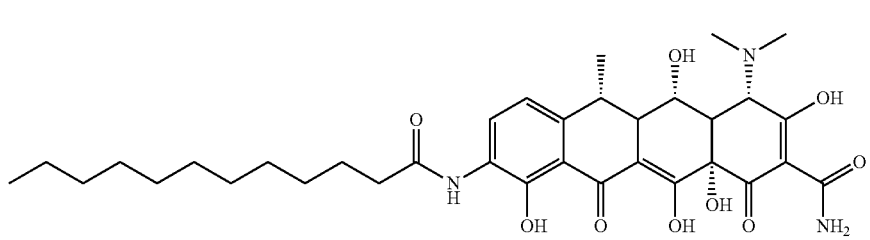

[19]

Example 3—A conjugate of doxycycline and a fatty acid. (4S,5S,6R,12aS)-4-(dimethylamino)-9-(dodecanoylamino)-3,5,10,12,12a-pentahydroxy-6-methyl-1,11-dioxo-4a,5,5a, 6-tetrahydro-4H-tetracene-2-carboxamide. Compound [20], shown below, was prepared following the method in Example 1. LC-MS 642.1 [M+H]+, RT 2.42 min.

decan-15-one. Compound [22] was prepared according to Vujasinovic, Ines et al. Novel tandem Reaction for the Synthesis of N'-Substituted 2-Imino-1,3-oxazolidines from Vicinal (sec-or tert-)Amino Alcohol of Desosamine. Eur. J. Org. Chem. 2011, 2507-2518. LC-MS 735.3 [M+H]+, RT 0.97 min.

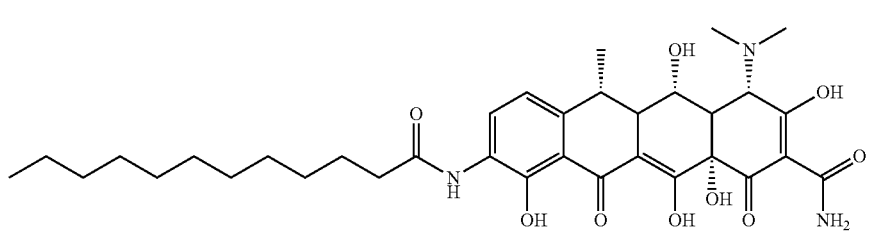

[20]

Example 4—A conjugate of doxycycline and TPP (as an oxalate salt). [6-[[(5R,6S,7S,10aS)-9-carbamoyl-7-(dimethylamino)-1,6,8,10a,11-pentahydroxy-5-methyl-10,12-dioxo-5a,6,6a,7-tetrahydro-5H-tetracen-2-yl]amino]-6-oxohexyl]-triphenyl-phosphonium oxalate. Compound [21], shown below, was prepared following the method in Example 1 except purified by preparative HPLC (Method B). LC-MS 409.7 [M½]+, RT 1.53 min.

[21]

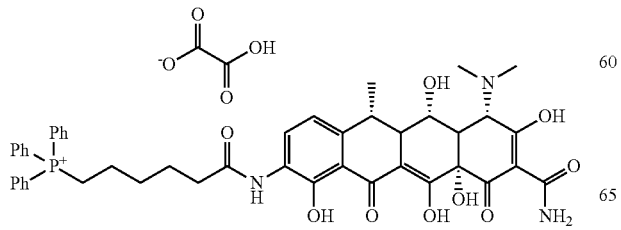

[22]

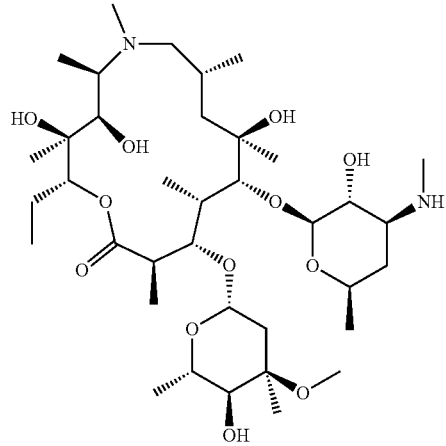

Example 6—An azithromycin-fatty acid conjugate. N-[(2S,3R,4S,6R)-2-[ [(2R,3S,4R,5R,8R,10R,11R,12S,13S, 14R)-2-ethyl-3,4,10-trihydroxy-13-[(2S,4R,5S,6S)-5-hydroxy-4-methoxy-4,6-dimethyl-tetrahydropyran-2-yl] oxy-3,5,6,8,10,12,14-heptamethyl-15-oxo-1-oxa-6-azacyclopentadec-11-yl]oxy]-3-hydroxy-6-methyl-tetrahydropyran-4-yl]-N-methyl-tetradecanamide.
Compound [23] was prepared from 2R,3S,4R,5R,8R,10R, 11R,12S,13S,14R)-2-ethyl-3,4,10-trihydroxy-13-[(2S,4R, 5S,6S)-5-hydroxy-4-methoxy-4,6-dimethyl-tetrahydropyran-2-yl]oxy-11-[(2S,3R,4S,6R)-3-hydroxy-6-methyl-4-(methylamino)tetrahydropyran-2-yl]oxy-3,5,6,8,10,12,14-heptamethyl-1-oxa-6-azacyclopentadecan-15-one following the method in Example 1 except using HCTU in place of HBTU and performing the final purification on silica gel (2.5% $NH_3$ in MeOH (7M)/DCM). LC-MS 946.4 $[M+H]^+$, RT 2.48 min.

to at least one of chemotherapeutic agents, natural substances, and caloric restriction.

Embodiments of the present approach may also take the form of methods for treating at least one of senescence, tumor recurrence, metastasis, drug resistance, cachexia, and radiotherapy resistance. It should be appreciated that the present approach may be used to provide compounds for the preparation of medicaments for treating at least one of senescence, tumor recurrence, metastasis, drug resistance, cachexia, and radiotherapy resistance. In some embodiments, methods according to the present approach may be administered following a conventional cancer treatment. In other embodiments, the present approach may precede a conventional cancer treatment, such as, for example, to prevent or reduce the likelihood of recurrence, metastasis,

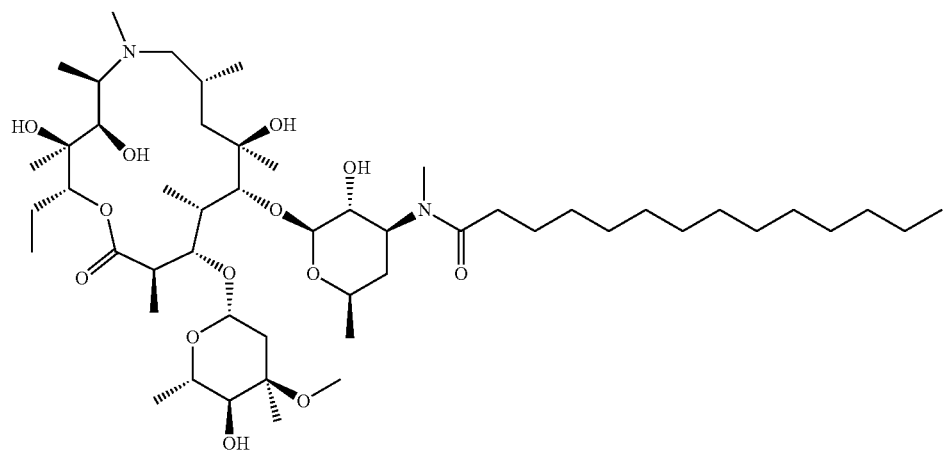

[23]

In some embodiments, one or more of the therapeutic agents may be part of an inclusion complex with a cyclodextrin compound, such as an alpha-cyclodextrin, beta-cyclodextrin, a gamma-cyclodextrin, and derivatives thereof. In some embodiments, the cyclodextrin derivative may include one or more of the targeting signals described in the prior paragraph. In some embodiments, a cyclodextrin inclusion complex may increase the delivery of the therapeutic agent to the target tissue. In some embodiments, the therapeutic agents may be contained in a kit, having the appropriate number of doses for each therapeutic agent for a given time period (e.g., one week, one month, etc.), in a pre-packaged container. For example, FIG. 18 shows kit 1801 with 2 doses of a first therapeutic agent, azithromycin ("Azith"), 14 doses of a second therapeutic agent, doxycycline ("Doxy"), and 7 doses of Vitamin C ("Vit C") in a blister pack. The example shown in FIG. 18 may be sufficient for one week of treatment, each vertical column representing a day of therapeutic agents. Of course, the contents of a particular kit may vary, depending on the selected doses, the treatment duration, and the like, for a particular embodiment.

It should be appreciated that embodiments of the present approach may possess advantageous benefits in addition to anti-aging and anti-cancer activity. In some embodiments, for example, the composition possesses at least one of radiosensitizing activity and photosensitizing activity. In some embodiments, the composition sensitizes cancer cells and/or resistance. In other embodiments, the present approach may be used in conjunction with a conventional cancer treatment.

The following paragraphs describe the methods and materials used in connection with the laboratory results and analysis provided above. Cell Lines and Reagents: MCF7 cells, an ER(+) human breast cancer cell line, was originally purchased from the American Type Culture Collection (ATCC), catalogue number HTB-22. Doxycycline, Azithromycin and Ascorbic Acid (Vitamin C) were obtained commercially from Sigma-Aldrich, Inc.

Mammosphere Formation Assay: A single cell suspension was prepared using enzymatic (1x Trypsin-EDTA, Sigma Aldrich, #T3924), and manual disaggregation (25 gauge needle). Cells were plated at a density of 500 cells/cm2 in mammosphere medium (DMEM-F12+B27+20 ng/ml EGF+ PenStrep) under non-adherent conditions, in culture dishes pre-coated with (2-hydroxyethylmethacrylate) (poly-HEMA, Sigma, #P3932), called "tumor-sphere plates". Vehicle alone (DMSO) control cells were processed in parallel. Cells were grown for 5 days and maintained in a humidified incubator at 37° C. After 5 days of culture, 3D mammospheres >50 μm were counted using an eye piece ("graticule"), and the percentage of cells plated which formed spheres was calculated and is referred to as percent mammosphere formation (MFE, and was normalized to one (1=100% MSF).

Metabolic Flux Analysis: Real-time oxygen consumption rates (OCR) and extracellular acidification rates (ECAR)

rates in MCF7 cells were determined using the Seahorse Extracellular Flux (XFe96) analyzer (Seahorse Bioscience, USA). Briefly, 1.5×104 cells per well were seeded into XFe96 well cell culture plates, and incubated overnight to allow cell attachment. Then, cells were treated with antibiotics for 72 h. Vehicle-alone control cells were processed in parallel. After 72 hours of incubation, cells were washed in pre-warmed XF assay media (or for OCR measurement, XF assay media supplemented with 10 mM glucose, 1 mM Pyruvate, 2 mM L-glutamine and adjusted at 7.4 pH). Cells were then maintained in 175 μL/well of XF assay media at 37° C., in a non-CO2 incubator for 1 hour. During the incubation time, we loaded 25 μL of 80 mM glucose, 9 μM oligomycin, and 1M 2-deoxyglucose (for ECAR measurement) or 10 μM oligomycin, 9 μM FCCP, 10 μM rotenone, 10 μM antimycin A (for OCR measurement), in XF assay media into the injection ports in the XFe96 sensor cartridge. Measurements were normalized by protein content (Bradford assay). Data sets were analyzed using XFe96 software and GraphPad Prism software, using one-way ANOVA and Student's t-test calculations. All experiments were performed in quintuplicate, three times independently.

Live/Dead Assay for Anoikis-Resistance: Following monolayer treatment with either Doxycycline alone, Azithromycin alone or the combination for 48 hours, the CSC population was enriched by seeding onto low-attachment plates. Under these conditions, the non-CSC population undergoes anoikis (a form of apoptosis induced by a lack of cell-substrate attachment) and CSCs are believed to survive. The surviving CSC fraction was then determined by FACS analysis. Briefly, 1×104 MCF7 monolayer cells were treated with antibiotics or vehicle alone for 48 h in 6-well plates. Then, cells were trypsinized and seeded in low-attachment plates in mammosphere media. After 12 h, the MCF7 cells were spun down. Cells were rinsed twice and incubated with LIVE/DEAD dye (Fixable Dead Violet reactive dye; Invitrogen) for 10 minutes. Samples were then analyzed by FACS (Fortessa, BD Bioscence). The live population was then identified by employing the LIVE/DEAD dye staining assay. Data were analyzed using FlowJo software.

The terminology used in the description of embodiments of the present approach is for the purpose of describing particular embodiments only and is not intended to be limiting. As used in the description and the appended claims, the singular forms "a," "an" and "the" are intended to include the plural forms as well, unless the context clearly indicates otherwise. The present approach encompasses numerous alternatives, modifications, and equivalents as will become apparent from consideration of the following detailed description.

It will be understood that although the terms "first," "second," "third," "a)," "b)," and "c)," etc. may be used herein to describe various elements of the present approach, and the claims should not be limited by these terms. These terms are only used to distinguish one element of the present approach from another. Thus, a first element discussed below could be termed an element aspect, and similarly, a third without departing from the teachings of the present approach. Thus, the terms "first," "second," "third," "a)," "b)," and "c)," etc. are not intended to necessarily convey a sequence or other hierarchy to the associated elements but are used for identification purposes only. The sequence of operations (or steps) is not limited to the order presented in the claims.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. All publications, patent applications, patents and other references mentioned herein are incorporated by reference in their entirety. In case of a conflict in terminology, the present specification is controlling.

Also, as used herein, "and/or" refers to and encompasses any and all possible combinations of one or more of the associated listed items, as well as the lack of combinations when interpreted in the alternative ("or").

Unless the context indicates otherwise, it is specifically intended that the various features of the present approach described herein can be used in any combination. Moreover, the present approach also contemplates that in some embodiments, any feature or combination of features described with respect to demonstrative embodiments can be excluded or omitted.

As used herein, the transitional phrase "consisting essentially of" (and grammatical variants) is to be interpreted as encompassing the recited materials or steps "and those that do not materially affect the basic and novel characteristic(s)" of the claim. Thus, the term "consisting essentially of" as used herein should not be interpreted as equivalent to "comprising."

The term "about," as used herein when referring to a measurable value, such as, for example, an amount or concentration and the like, is meant to encompass variations of ±20%, ±10%, ±5%, ±1%, ±0.5%, or even ±0.1% of the specified amount. A range provided herein for a measurable value may include any other range and/or individual value therein.

Having thus described certain embodiments of the present approach, it is to be understood that the scope of the appended claims is not to be limited by particular details set forth in the above description as many apparent variations thereof are possible without departing from the spirit or scope thereof as hereinafter claimed.

What is claimed is:

1. A method for treating the effects of aging, the method comprising: simultaneously (a) administering to the patient in need thereof an effective amount of a first therapeutic agent that inhibits mitochondrial biogenesis and targets the large mitochondrial ribosome, (b) administering an effective amount of a second therapeutic agent that inhibits mitochondrial biogenesis and targets the small mitochondrial ribosome, and (c) inducing mitochondrial oxidative stress through either a third therapeutic agent or radiation treatment; wherein at least one therapeutic agent comprises a conjugate with a TPP moiety.

2. The method of claim 1, wherein the first therapeutic agent comprises azithromycin, the second therapeutic agent comprises doxycycline, and inducing mitochondrial oxidative stress comprises administering Vitamin C.

3. The method of claim 2, wherein the azithromycin is present at 250 mg, and the doxycycline is present at 20 mg to 100 mg.

4. The method of claim 1, wherein mitochondrial oxidative stress is induced by a third therapeutic agent comprising at least one of Vitamin C and ascorbyl palmitate, the first therapeutic agent comprises an erythromycin family member conjugated with a first fatty acid, and the second therapeutic agent comprises a tetracycline family member conjugated with a second fatty acid.

5. The method of claim 4, wherein at least one of the first fatty acid and the second fatty acid comprises myristic acid.

6. The method of claim 1, wherein at least one therapeutic agent comprises a conjugate with a fatty acid moiety.

7. The method of claim 1, wherein the first therapeutic agent comprises an azithromycin and myristic acid conjugate, and the second therapeutic agent comprises a doxycycline and myristic acid conjugate.

8. The method of claim 1, wherein mitochondrial oxidative stress in the cancer cells is induced by one of radiation therapy, and a third therapeutic agent comprising at least one of Vitamin C and ascorbyl palmitate.

9. An anti-aging therapeutic method comprising targeting and inhibiting senescent cells in a patient by simultaneously:
inhibiting mitochondrial biogenesis in the senescent cells with a first therapeutic agent that targets the large mitochondrial ribosome,
inhibiting mitochondrial biogenesis in the senescent cells with a second therapeutic agent and targets the small mitochondrial ribosome, and
inducing mitochondrial oxidative stress in the senescent cells with a third therapeutic agent;
wherein at least one therapeutic agent comprises a conjugate with a TPP moiety.

10. The method of claim 9, wherein the first therapeutic agent comprises azithromycin, the second therapeutic agent comprises doxycycline, and the third therapeutic agent comprises Vitamin C.

11. The method of claim 10, wherein the azithromycin is present at 250 mg and the doxycycline is present at 20 mg to 100 mg.

12. The method of claim 9, wherein the third therapeutic agent is at least one of Vitamin C, an ascorbate derivative, a chemotherapeutic, and radiation.

13. The method of claim 9, wherein the first therapeutic agent comprises a conjugate of azithromycin and a first fatty acid, the second therapeutic agent comprises a conjugate of doxycycline and a second fatty acid, and the third therapeutic agent comprises at least one of Vitamin C, ascorbyl palmitate, and an ascorbate derivative.

14. The method of claim 13, wherein at least one of the first fatty acid and the second fatty acid is myristic acid.

15. A method for delaying the onset of senescence in a patient, the method comprising: inhibiting mitochondrial biogenesis in a plurality of senescent cells in the patient with a first therapeutic agent that targets the large mitochondrial ribosome, inhibiting mitochondrial biogenesis in the plurality of senescent cells with a second therapeutic agent and targets the small mitochondrial ribosome, and inducing mitochondrial oxidative stress in the plurality of senescent cells with a third therapeutic agent; wherein at least one therapeutic agent comprises a conjugate with a TPP moiety; and wherein the first therapeutic agent, the second therapeutic agent, and the third therapeutic agent are administered simultaneously to the patient.

16. The method of claim 15, wherein the first therapeutic agent is one of azithromycin and a conjugate of azithromycin and a first fatty acid, the second therapeutic agent is one of doxycycline and a conjugate of doxycycline and a second fatty acid, and the third therapeutic agent is one of Vitamin C, ascorbyl palmitate, and an ascorbate derivative.

* * * * *